(12) United States Patent
Van Der Mooren et al.

(10) Patent No.: US 8,702,639 B2
(45) Date of Patent: Apr. 22, 2014

(54) GLAUCOMA SHUNTS WITH FLOW MANAGEMENT AND IMPROVED SURGICAL PERFORMANCE

(75) Inventors: Marrie H. Van Der Mooren, Engelbert (NL); Theophilus Bogaert, Groningen (NL); Rakhi Jain, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 469 days.

(21) Appl. No.: 12/732,030

(22) Filed: Mar. 25, 2010

(65) Prior Publication Data

US 2010/0249691 A1 Sep. 30, 2010

Related U.S. Application Data

(60) Provisional application No. 61/163,862, filed on Mar. 26, 2009.

(51) Int. Cl.
*A61M 5/00* (2006.01)

(52) U.S. Cl.
USPC .............. 604/8; 604/294; 606/4; 606/6

(58) Field of Classification Search
USPC .............. 604/8–10, 264, 294; 606/4–6
See application file for complete search history.

(56) References Cited

U.S. PATENT DOCUMENTS

| | | | |
|---|---|---|---|
| 1,246,971 | A | 11/1915 | Maier |
| 2,969,066 | A | 10/1956 | Holter et al. |
| 3,109,429 | A | 11/1963 | Schwartz |
| 3,159,161 | A | 12/1964 | Ness |
| 3,527,226 | A | 9/1970 | Hakim |
| 3,726,284 | A | 4/1973 | Parker |
| 3,788,327 | A | 1/1974 | Donowitz et al. |
| 3,860,008 | A | 1/1975 | Miner et al. |

(Continued)

FOREIGN PATENT DOCUMENTS

| | | |
|---|---|---|
| EP | 0102747 | 3/1984 |
| EP | 0168201 | 1/1986 |

(Continued)

OTHER PUBLICATIONS

International Search Report for Application No. PCT/US2010/028722, mailed on Feb. 10, 2011, 8 pages.

(Continued)

*Primary Examiner* — Melanie Hand
(74) *Attorney, Agent, or Firm* — Abbott Medical Optics Inc.

(57) ABSTRACT

A method of treating glaucoma in an eye by managing fluid flow past an implanted shunt having an elastomeric plate and a non-valved elastomeric drainage tube. The plate is positioned over a sclera of the eye with an outflow end of the elastomeric drainage tube open to an outer face of the plate. An inflow end of the drainage tube tunnels through the sclera to the anterior chamber of the eye. The plate may have regions of greater propensity for cell adhesion alternating with regions of lesser cell adhesion. For example, regions of texturing around the plate or drainage tube may be provided to control the size of a bleb that forms over the implant. The effective surface area of the plate may be balanced against a number of fenestrations. The drainage tube has a reduced profile and may be shaped with a non-circular external cross-section to reduce its height. A scleral groove may be used to further reduce the height of the drainage tube on the sclera. A flow restrictor for the early post operative period will immediately lower the intraocular pressure (IOP) and simultaneously prevent hypotony.

15 Claims, 9 Drawing Sheets

(56) References Cited

U.S. PATENT DOCUMENTS

| | | | |
|---|---|---|---|
| 3,915,172 | A | 10/1975 | Wichterle et al. |
| 4,030,480 | A | 6/1977 | Meyer |
| 4,240,434 | A | 12/1980 | Newkirk |
| 4,298,994 | A | 11/1981 | Clayman |
| 4,373,218 | A | 2/1983 | Schachar |
| 4,402,681 | A | 9/1983 | Haas et al. |
| 4,428,746 | A | 1/1984 | Mendez |
| 4,457,757 | A | 7/1984 | Molteno |
| 4,521,210 | A | 6/1985 | Wong |
| 4,604,087 | A | 8/1986 | Joseph |
| 4,634,418 | A | 1/1987 | Binder |
| 4,722,724 | A | 2/1988 | Schocket |
| 4,729,761 | A | 3/1988 | White |
| 4,750,901 | A | 6/1988 | Molteno |
| 4,767,400 | A | 8/1988 | Miller et al. |
| 4,836,457 | A | 6/1989 | Greiner |
| 4,863,457 | A | 9/1989 | Lee |
| 4,865,601 | A | 9/1989 | Caldwell et al. |
| 4,886,488 | A | 12/1989 | White |
| 4,902,292 | A | 2/1990 | Joseph |
| 4,915,684 | A | 4/1990 | MacKeen et al. |
| 4,932,968 | A | 6/1990 | Caldwell et al. |
| 4,936,825 | A | 6/1990 | Ungerleider |
| 4,946,436 | A | 8/1990 | Smith |
| 4,955,909 | A | 9/1990 | Ersek et al. |
| 4,968,296 | A | 11/1990 | Ritch et al. |
| 5,092,837 | A | 3/1992 | Ritch et al. |
| 5,171,213 | A | 12/1992 | Price |
| 5,178,604 | A | 1/1993 | Baerveldt et al. |
| 5,192,315 | A | 3/1993 | Jacob-LaBarre |
| 5,282,851 | A | 2/1994 | Jacob-LaBarre |
| 5,300,020 | A | 4/1994 | L'Esperance, Jr. |
| 5,338,291 | A | 8/1994 | Speckman et al. |
| 5,372,577 | A | 12/1994 | Ungerleider |
| 5,397,300 | A | 3/1995 | Baerveldt et al. |
| 5,476,445 | A | 12/1995 | Baerveldt et al. |
| 5,549,670 | A | 8/1996 | Young et al. |
| 5,558,629 | A | 9/1996 | Baerveldt et al. |
| 5,704,907 | A | 1/1998 | Nordquist et al. |
| 5,725,493 | A | 3/1998 | Avery et al. |
| 5,882,327 | A | 3/1999 | Jacob |
| 6,050,970 | A | 4/2000 | Baerveldt |
| 6,203,513 | B1 | 3/2001 | Yaron et al. |
| 6,984,392 | B2 | 1/2006 | Bechert et al. |
| 7,160,264 | B2 | 1/2007 | Lisk, Jr. et al. |
| 7,207,965 | B2 | 4/2007 | Simon |
| 7,220,238 | B2 | 5/2007 | Lynch et al. |
| 7,297,130 | B2 | 11/2007 | Bergheim et al. |
| 7,357,778 | B2 | 4/2008 | Bhalla |
| 7,476,698 | B2 | 1/2009 | Wagener et al. |
| 7,547,302 | B2 | 6/2009 | Porto et al. |
| 7,635,358 | B2 | 12/2009 | Tan |
| 7,641,627 | B2 | 1/2010 | Camras et al. |
| 2005/0107734 | A1 | 5/2005 | Coroneo |
| 2005/0125003 | A1 | 6/2005 | Pinchuk et al. |
| 2005/0267398 | A1 | 12/2005 | Protopsaltis et al. |
| 2007/0293872 | A1 | 12/2007 | Peyman |
| 2008/0077071 | A1 | 3/2008 | Yaron |
| 2008/0077238 | A1 | 3/2008 | Deacon et al. |
| 2008/0200860 | A1 | 8/2008 | Tu et al. |

FOREIGN PATENT DOCUMENTS

| | | |
|---|---|---|
| FR | 2233028 | 1/1975 |
| GB | 2101891 | 1/1983 |
| GB | 2160778 | 1/1986 |
| GB | 2187963 | 9/1987 |
| RU | 906561 | 2/1982 |
| WO | 9112037 | 8/1991 |
| WO | 9112046 | 8/1991 |
| WO | 9118568 | 12/1991 |
| WO | WO9118586 A1 | 12/1991 |
| WO | 9320783 | 10/1993 |
| WO | 9402081 | 2/1994 |
| WO | 2006012009 A2 | 2/2006 |
| WO | 2007087061 | 8/2007 |

OTHER PUBLICATIONS

Rauscher F.M., et al., "Long-term Outcomes of Amniotic membrane Transplantation for Repair of Leaking Glaucoma Filtering Blebs", American Journal of Opthammology, 2007, pp. 1052-1054.

Mokwa in "Ophthalmic Implants," 2003 IEEE Publication, 980-986, Institute of Materials in Electrical Engineering, RWTH Aachen Univ., Aachen, Germany.

Kakaday, et al. in "Advances in Telemetric Continuous Intraocular Pressure Assessment<" British Journal of Ophthalmology, 2009; 93:992-996.

Krupin, at al., "Filtering Valve Implant Surgery for Eyes with Neovascular Glaucoma." American Journal of Ophthalology, vol. 89, No. 3, 1980, pp. 338-343.

Lee, et al., "Aqueous-Venous Shunt for Glaucoma," Arch Ophthalmol, vol. 99, Nov. 1981, pp. 2007-2012.

Molteno, "Use of Molteno Implants to Treat Secondary Claucoma," Glaucoma, Grune & Stratton, Ltd., 1986, pp. 211-238.

Bickford, "Molteno Implant System, for Patient wth Previously Unsuccessful Glaucoma Surgery," Journal of Ophthalmic Nursing & Technology, vol. 6, 1987, pp. 224-229.

Minckler, et al., "Clinical Experience with the Single-Plate Molteno Implant in Complicated Glaucomas," Ophthalmolgy News, vol. 95, No. 9, Sep. 1988, pp. 1181-1188.

"Experience with Molteno-Type Shunts . . . ," Ocular Surgery News, Jun. 1, 1989, pp. 27-29.

Davidovski, et al., "Long-Term Results with the White Glaucoma Pump-Shunt," Ophthalmic Surgery, vol, No. 4, 1990, pp. 288-293.

White, "A New Implantable Ocular Pressure Relief Device," University of South Dakota Medical School, Sioux Falls, San Diego, one page.

"Molteno Seton Implant, for Management of Refractory Glaucoma," Staar Surgical Company, Monrovia, California, one page brochure.

Alder "Intraocular Pressure," Alder's Physiology of the Eye, Chapter 5, pp. 249-277.

GLAUCOMA SHUNTS WITH FLOW MANAGEMENT AND IMPROVED SURGICAL PERFORMANCE

RELATED APPLICATIONS

The present application claims priority under 35 U.S.C. §119(e) to Provisional Application No. 61/163,862, filed on Mar. 26, 2009.

FIELD OF THE INVENTION

The present invention relates to treatments for glaucoma in the eye and, more particularly, to glaucoma shunts and methods of use for draining fluid from the eye at a controlled rate.

BACKGROUND OF THE INVENTION

Intraocular pressure in the eye is maintained by the formation and drainage of aqueous humor, a clear, colorless fluid that fills the anterior and posterior chambers of the eye. Aqueous humor normally flows from the anterior chamber of the eye out through an aqueous outflow channel at a rate of 2 to 3 microliters per minute.

Glaucoma is a progressive disease of the eye characterized by a gradual increase of intraocular pressure (IOP). This increase in pressure is most commonly caused by stenosis or blockage of the aqueous outflow channel, resulting in excessive buildup of aqueous fluid within the eye. Other causes include increase in venous pressure outside the eye which is reflected back through the aqueous drainage channels and increased production of aqueous humor. In a "normal" eye, IOP ranges from 8 to 21 mm mercury. In an eye with glaucoma, IOP can range between normal pressures up to as much as 50 mm mercury. This increase in IOP produces gradual and permanent loss of vision in the afflicted eye.

Existing corrective methods for the treatment of glaucoma include drugs, surgery, and implants. Pharmacological treatment is prohibitively expensive to a large majority of glaucoma patients. In addition, many people afflicted with the disease live in remote or undeveloped remote areas where the drugs are not readily accessible. The drugs used in the treatment, in particular steroids, often have undesirable side effects and many of the long-term effects resulting from prolonged use are not yet known. Additionally, patient compliance is an issue and, for example, patients often forget their medication.

Surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous humor free passage from the posterior to the anterior chambers in the eye. A trabeculotomy, opening the inner wall of Schlemm's canal, is often performed in cases of developmental or juvenile glaucoma so as to increase the outflow of the aqueous humor, thereby decreasing IOP. In adults, a trabeculectomy shunts fluid through a trap-door flap in the eye that performs a valve-like function for the first few weeks after surgery.

While often successful, these surgical techniques possess inherent risks associated with invasive surgery on an already afflicted or compromised eye. Furthermore, the tissue of the eye can scar over this small area and the eye reverts to the pre-operative condition, thereby necessitating the need for further treatment.

Ocular implants are often used in long-term glaucoma treatment. One early implant is described in the paper entitled "Use of Molteno Implants to Treat Secondary Glaucoma" by A. C. B. Molteno and published by Grune & Stratton, Ltd, 1986, pp 211-238. The implant was a small circular plate with a rigid translimbal drainage tube attached thereto. The plate was 8.5 mm in diameter and formed a surface area of about 100 $mm^2$. This early Molteno implant was sutured to the sclera in the anterior segment of the eye at the limbus and the drainage tube was inserted into the anterior chamber of the eye. Once implanted, the body forms scar tissue around this plate. Fluid causes the tissues above the plate to lift and form a bleb into which aqueous humor flows from the anterior chamber via the drainage tube. A bleb is a fluid filled space surrounded by scar tissue, somewhat akin to a blister. The fluid within the bleb then flows through the scar tissue, at a rate which desirably regulates IOP.

Many problems occurred with the early Molteno device. The bleb that formed on the sclera was elevated, which resulted in Dellen formation (sterile corneal ulcers). The implant sometimes had to be removed in another surgery to cure the ulcers. Further, this early device often did not reduce the IOP enough to treat the glaucoma without the use of additional medications.

Dr. Molteno redesigned his implant for insertion into the posterior segment of the eye to avoid the problems with his early anterior device, as disclosed in U.S. Pat. No. 4,457,757 entitled "Device for Draining Aqueous Humor." This implant is commercially available as the Molteno® Seton Implant and is also referred to as the long tube Molteno implant. The implant comprises a flexible drainage tube connected to one or more rigid plate reservoirs. The plates are shaped to conform to the curvature of the eye. The long tube Molteno implant is disadvantageous as the plates are formed of a rigid plastic which makes insertion beneath the eye tissue difficult and time-consuming. The reservoir plate is placed under Tenon's capsule in the posterior segment of the eye and sutured to the sclera. The drainage tube is implanted into the anterior chamber through a scleral incision.

After a glaucoma implant is attached, IOP tends to fall as aqueous fluid flows immediately through the drainage tube. An open drainage tube may release too much of the fluid too fast, which is detrimental to the eye. It is not until 2-6 weeks later that the bleb forms around the plate to sufficiently regulate the fluid flow. Some prior devices have therefore incorporated valves in the fluid drain path designed to function for a limited time until the bleb forms. However, such valved devices sometimes clog later, requiring another surgery.

More recently, U.S. Pat. Nos. 5,476,445 and 6,050,970 to Dr. George Baerveldt, et al. disclose glaucoma implants or shunts featuring a flexible plate that attaches to the sclera and a drainage tube positioned for insertion into the anterior chamber of the eye. A bleb forms around the plate and fluid drains into and out of the bleb to regulate IOP. This type of shunt is sold under the tradename Baerveldt® BG Series of glaucoma implants by Abbott Medical Optics (AMO) of Santa Ana, Calif. The Baerveldt® device has an open tube with no flow restricting elements. Temporary sutures are used to restrict fluid flow for a predetermined period after which the bleb forms and fluid drainage is properly regulated. The temporary sutures are either biodegradable or removed in a separate procedure. This method works well, but the timing of suture dissolution is necessarily inexact, and a second procedure undesirable.

The Baerveldt® shunts also include four fenestrations (perforations or holes) through the plate to promote fibrous adhesion, which may reduce bleb height. Though a bleb is thought to have a beneficial function in regulating aqueous humor diffusion, too large of a bleb may cause the patient some pain or may be aesthetically unacceptable. Some doctors even prefer to use anti-proliferatives such as mitomycin C or 5-FU at the time of surgery to prevent formation of the fibrous bleb. Another potential complication is endophthalmitis, or an inflammation of the internal tissue of the eye. This complication may occur in any intraocular surgery, with possible loss of vision and the eye itself. Infectious etiology is the most common cause, and various bacteria and fungi have been isolated as the cause of the endophthalmitis. The risk of infection is more pronounced early in a glaucoma shunt procedure when a passage to the interior of the eye is created and fluid flows therethrough. Later, a bleb forms which acts as a filter to prevent microorganisms such as bacteria from entering the eye.

Despite accepted treatments for regulation of intraocular pressure using glaucoma shunts, there is a need for an implant that better manages 1) the configuration of the bleb and attendant aqueous flow performance, and 2) flow performance directly after implantation and before bleb formation.

SUMMARY OF THE INVENTION

The present application provides various solutions for improving glaucoma shunts and reducing post-op complications. In a preferred embodiment, a glaucoma shunt having a pliable plate attached to the sclera and a drainage tube that extends into the inner eye causes a bleb to form around the plate which effectively regulates intraocular pressure (IOP). The pliable plate has a reduced size and may be microtextured in particular areas to control cell adhesion thereto. A flow restrictor within the drainage tube helps prevent excessive pressure buildup or dropoff immediately post-op, and an antimicrobial coating reduces the chance of infection.

In accordance with one aspect, an implantable glaucoma shunt for treating glaucoma in an eye includes a plate adapted to be positioned on the sclera, the plate having microtexturing on at least an outer or an inner face comprising an average peak-to-valley depth normal to the outer face of between about 0.5-10 microns. An elastomeric drainage tube has an outflow end that connects to the plate, opening at the outer face thereof, and an inflow end extending away from the plate. The drainage tube has an open lumen and a length sufficient to extend into the anterior chamber of the eye. The glaucoma shunt microtexturing may comprise surface features that collectively have an average peak-to-valley depth, an average width perpendicular to the depth, and an average pitch separating individual features, all of which are between about 0.5-10 microns. For instance, the average peak-to-valley depth may be about 0.5 microns and the average pitch separating individual features about 4 microns. In one embodiment, the microtexturing comprises uniform, regular shaped elements with sharp corners, or the microtexturing elements may be selected from the group consisting of grooves, ridges, wells, and pillars.

In a preferred embodiment, the plate has a concave inner face and a convex outer face, and further includes a plurality of fenestrations extending therethrough from the inner face to the outer face. Both the inner and outer faces may have the microtexturing, which may be provided in different patterns on the inner and outer faces. In one version, the microtexturing encircles the fenestrations within radii of about 1 mm to about 5 mm. The microtexturing may also be located on the periphery of the outer face of the plate, or the microtexturing may be only on the periphery of the outer face of the plate. Desirably, the microtexturing promotes cell adhesion with adjacent tissue and is located in a pattern that channels allowing fluid flow between regions with microtexturing. The plate may further include a chemical coating to promote cellular adhesion, which may be selected from the group consisting of polyethylene glycol (PEG), heparin, nano-coatings of titanium selectively sputter-coated, silicone oxide, and silicone oxide with polyethylene glycol. In another embodiment, the microtexturing is further provided on the exterior of the elastomeric drainage tube.

Another aspect of the present invention is an implantable glaucoma shunt for treating glaucoma in an eye which has a plate adapted to be positioned on the sclera having on at least an outer face cell adhesion regions with increased propensity for cell adhesion alternating with surface regions that have relatively lower propensity for cell adhesion. An elastomeric drainage tube has an outflow end that connects to the plate, opening at the outer face thereof, and an inflow end extending away from the plate. The drainage tube has an open lumen and a length sufficient to extend into the anterior chamber of the eye. The surface regions may form interconnected channels that isolate at least one of the cell adhesion regions from the other cell adhesion regions. Desirably, the cell adhesion regions comprise regions of texturing, and in particular may comprise microtexturing having an average peak-to-valley depth normal to the outer face of between about 0.5-10 microns. The microtexturing may comprise uniform, regular shaped elements with sharp corners. Alternatively, the cell adhesion regions comprise regions of chemical coating.

Another implantable glaucoma shunt for treating glaucoma in an eye disclosed herein features a plate adapted to be positioned on the sclera, and an elastomeric drainage tube. The tube has an outflow end connected to the plate, opening at the outer face thereof, and an inflow end extending away from the plate. The drainage tube further has an open lumen and a length sufficient to extend into the anterior chamber of the eye. The exterior of the drainage tube near the outflow end has microtexturing thereon with an average peak-to-valley depth normal to the exterior of between about 0.5-10 microns.

A still further implantable glaucoma shunt for treating glaucoma in an eye of the present application, comprises a plate adapted to be positioned on the sclera and having an effective surface area $A_{eff}$ of 250 mm$^2$ or less. The plate also has at least 8 fenestrations extending between an outer face and an inner face. An elastomeric drainage tube has an outflow end that connects to the plate, opening at the outer face thereof, and an inflow end extending away from the plate. The drainage tube has an open lumen and a length sufficient to extend into the anterior chamber of the eye. The effective surface area $A_{eff}$ of the plate may be determined by the formula A+G, where:

A=the tissue surface area surrounding the plate within its periphery, and

G=a reduction in plate effective surface area determined by:

$$G = M(\pi R^2) - M(2\pi RB)$$

and where:

M=number of fenestration holes,

R=radius of fenestration holes, and

B=bleb height.

Currently, a good estimation is that the tissue surface area A surrounding the plate within its periphery should be around 200-400 mm$^2$ (based on the satisfactory clinical use of the Baerveldt® BG Series shunt having plate areas of 250 mm$^2$ and 350 mm$^2$). Also, a maximum reduction in plate surface will be reached if radius of fenestration hole is identical to the bleb height.

In accordance with a still further aspect of the application, an implantable glaucoma shunt for treating glaucoma in an eye includes a plate adapted to be positioned on the sclera, and an elastomeric drainage tube having an outflow end connected to the plate, opening at the outer face thereof, and an inflow end extending away from the plate. The drainage tube has an open lumen and a length sufficient to extend into the anterior chamber of the eye, the inner lumen of the tube having a radius of less than 50 microns. The inner tube lumen radius is desirably less than 50 microns and greater than or equal to a magnitude determined by the following formula:

$$r = (8\eta L/\pi R)^{0.25}$$

where:

average aqueous resistance R=3.333 mmHg/microliter/minute, 1 mmHg=133.3 Pa (kgm/s$^2$), 1 microliter/minute=1.667×10$^{-11}$ m$^3$/s, L=length of tube (mm), average aqueous resistance R=2.666×10$^{13}$ kg/sm$^2$, and dynamic viscosity η=7.50×10$^{-4}$ kg/sm.

A still further implantable glaucoma shunt for treating glaucoma in an eye described herein includes a plate adapted to be positioned on the sclera, and an elastomeric drainage tube. The tube has an outflow end connected to the plate and opens at the outer face thereof. An inflow end of the tube extends away from the plate, and the tube has an open lumen and a length sufficient to extend into the anterior chamber of the eye. Furthermore, the tube has a non-circular radial outer cross-section. For instance, the radial outer cross-section of the tube may be oval.

Another aspect of the application is an implantable glaucoma shunt for treating glaucoma in an eye including a plate adapted to be positioned on the sclera, and an elastomeric drainage tube having an outflow end connected to the plate and opening at the outer face thereof. An inflow end of the tube extends away from the plate, and the tube has a lumen and a length sufficient to extend into the anterior chamber of the eye. A flow restrictor positioned within the drainage tube has an open throughbore smaller than the lumen. The flow restrictor may be made of a material that may dissolve in aqueous fluid, or may be a non-dissolving material. In the latter embodiment, a short length of flow restrictor may be installed in the drainage tube and temporarily held in place by a fixation ligature. After the ligature resorbs or is removed, the flow restrictor migrates from fluid flow out of the tube and into the bleb.

A method of implanting a glaucoma shunt for treating glaucoma in an eye is also disclosed, and includes first providing a glaucoma shunt having a plate adapted to be positioned on the sclera and an elastomeric drainage tube having an outflow end connected to the plate and opening at the outer face thereof. The drainage tube also has an inflow end extending away from the plate, and a lumen and a length sufficient to extend into the anterior chamber of the eye. The method involves forming a groove in the sclera, attaching the shunt plate to the sclera, inserting the inflow end of the drainage tube through an incision into the eye, and positioning and securing a mid-portion of the drainage tube in the groove.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

Figure 1:
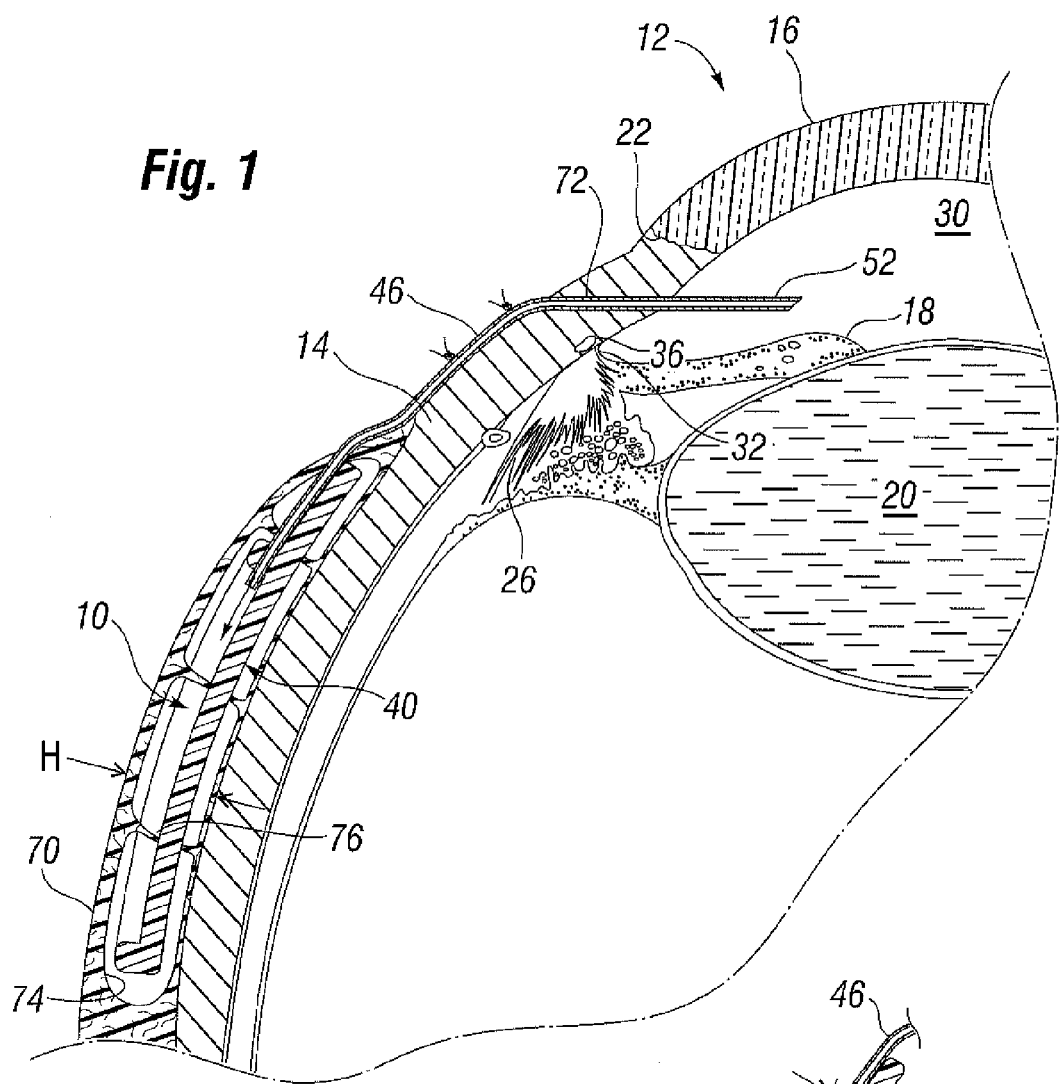
FIG. 1 is a cross-sectional view of the human eye which illustrates the glaucoma shunt of the present application after implant.

FIG. 1 illustrates a glaucoma shunt 10 constructed in accordance with the present application positioned within the tissue of an eye 12 (looking upward relative to the page). The relevant structures of the eye 12 will be described briefly below to provide background for the anatomical terms incorporated herein, however, it should be realized that a number of anatomical details have been omitted for clarity of understanding. The tough outer membrane known as the sclera 14 covers all of the eye 12 except that portion covered by the cornea 16, the thin, transparent membrane which enables light to enter the pupil 18 defined by the iris aperture in front of the lens 20. The cornea 16 merges into the sclera 14 at a juncture referred to as the limbus 22. The ciliary body 26 begins near the limbus 22 and extends along the interior of the sclera 14.

It is well-known that aqueous humor is produced by the ciliary body 26 and reaches the anterior chamber 30 formed between the iris 18 and the cornea 16 through the pupil. In a normal eye, most of the aqueous humor is removed through the trabecular meshwork 32, though there is also minor uveoscleral outflow. From there the aqueous humor passes through Schlemm's canal 36 and through veins which merge with blood-carrying veins and into venous circulation. Intraocular pressure is maintained in the eye 12 by the intricate balance of secretion and absorption or outflow of the aqueous humor in the manner described above. The condition of glaucoma results from excessive buildup of aqueous fluid in the anterior chamber 30 which produces an increase in intraocular pressure. The present invention is designed for treatment of glaucoma by facilitating the outflow of the aqueous humor from the anterior chamber 30 of the eye 12.

Figure 2:
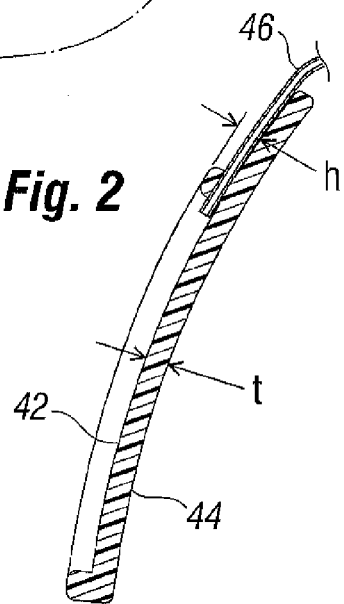
FIG. 2 is a cross-sectional view of the glaucoma shunt of FIG. 1.
Figure 3:
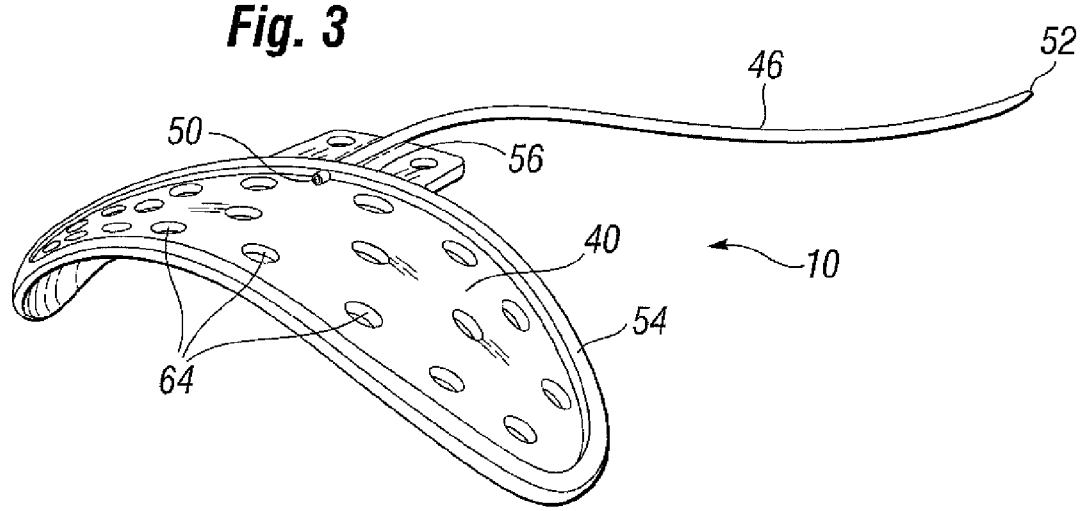
FIG. 3 is a perspective view of an exemplary glaucoma shunt disclosed herein having a plurality of fenestration holes and a raised peripheral ridge.
Figure 4:
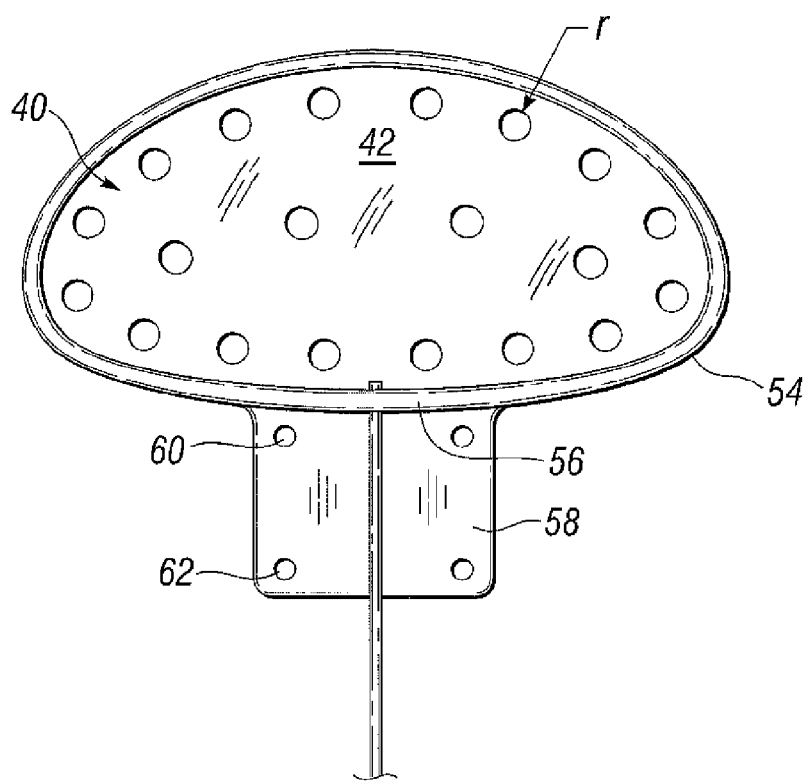
FIG. 4 is an outer face plan view of the glaucoma shunt of FIG. 3.

With reference to FIGS. 2-4 as well as FIG. 1, the glaucoma shunt 10 comprises a pliable plate 40, also referred to as a pliable seton in the ophthalmic field, having oppositely disposed convex outer 42 and concave inner 44 faces. The curvature of the plate 40 conforms to the sclera 14 and connects to a discharge or drainage tube 46 that extends into the anterior chamber 30 of the eye 12.

The plate 40 is preferably formed of silicone elastomer, such as SILASTIC®, Medical Grade Q7-4765, 65 Shore A, manufactured by Dow Corning Corporation of Midland, Mich. or Nusil Corp. of Santa Barbara, Calif., although other silicone elastomers in the range of 40-85 Shore A and having good elastic memory are also suitable. The silicone elastomer may be mixed or doped with a radiopaque material, such as Barium Sulfate, so that the implant is visible in X-rays procedures.

With reference now to FIGS. 3 and 4, elements of the glaucoma shunt 10 can be more clearly described. The drainage tube 46 comprises an outflow end 50 and an inflow end 52, wherein the outflow end 50 attaches to the plate 40 and opens to the outer face 42. The plate 40 has a generally spherical curvature with an elliptical perimeter looking down or in plan view, as in FIG. 4. The surface area of the plate 40 is preferably in the range of approximately 100 to 600 mm$^2$ depending on glaucoma conditions and the radius of curvature of the plate 40 is preferably 12-14 mm. An optional raised border 54 projects outward from the outer convex face 42 and extends around the perimetric edge of the plate 40. The inner face 44 of the plate 40 curves to conform to the curvature of the eye 12, specifically the curvature of the sclera 14, and the border 54 follows that curvature.

The thickness of the plate 40 in combination with the raised border 54 is desirably about 150-200% the thickness of the plate itself. The peripheral border 54 provides rigidity to the plate 40 to assist a surgeon to manipulate it through an incision and into proper placement. Moreover, the structural strength provided by the peripheral border 54 permits the central portion of the plate 40 to be made thinner, potentially 0.2 mm thinner than previous designs, or 10-50% thinner in relative terms. A thinner plate 40 forms a thinner bleb, which assists in the eventual pressure regulating function of the shunt 10. That is, a thicker bleb wall has a higher IOP in the eye. Conversely, reducing the bleb thickness increases outflow, which in turn decreases the ocular IOP. The precisely engineered plate 10 then governs the increased outflow of aqueous fluid.

The drainage tube 46 connects to the plate 40 with adhesive, such as Clear Silicone Rubber Adhesive RTV-118 manufactured by General Electric Silicone Products of Waterford, N.Y., via a small hole formed in a ridge 56. In the illustrated embodiment, the ridge 56 comprises a segment of the raised border 54, though in the absence of the border the ridge 56 would have a width similar to the width of a tab or extension 58 described below. The outflow end 50 of the tube 46 opens to and thus drains to the outer face 42 of the plate 40, and into the shallow outer recess circumscribed by the raised border 54.

The tab 58 of the shunt 10 formed adjacent the ridge 56 extends from one long side of the plate 40 and includes two pairs of suture holes 60, 62. The extension 58 is desirably larger in size than previous such tabs to facilitate implant. That is, the plate 40 can be positioned relatively far back around the eye 12 with the suture holes 60, 62 on the extension 58 plainly visible and accessible. In a preferred embodiment, the plate 40 attaches to the sclera such that the ridge 56, and thus the outflow end 50 of the drainage tube 46, is located between about 8-12 mm posteriorly from the limbus 22. To permit this desirable positioning, the extension 58 has a width of about 4-12 mm and a length of about 2-10 mm.

The plate 40 of the embodiment of FIGS. 3-4 includes a series of holes or fenestrations 64 from the outer face 42 through to the inner face 44. The fenestrations 64 permit aqueous fluid to pass from one side of the plate 40 to the other, and also tissue to form therethrough. In the illustrated embodiment there are sixteen fenestrations 64 spaced evenly around the periphery of the plate 40 just inside the border 54, and four spaced generally evenly across the middle portion of the plate. Of course, other arrangements of fenestrations are contemplated, as described below with reference to FIGS. 5A and 5B.

The present invention can be implanted using known opthalmological surgical techniques and, with reference to FIG. 1, the surgical implant procedure will be briefly described. It should be understood that the following procedure may be used for any of the exemplary glaucoma shunts described herein. An initial incision is made in the Tenon's capsule 70 parallel to the limbus 22. The plate 40 is inserted through the initial incision and positioned beneath the Tenon's capsule 70 and a portion of the rectus muscle (not shown) or extending totally under one or more muscles, thus covering the sclera 14. The plate 40 can be sutured to the sclera 14, or alternatively, to the rectus muscle if the sclera 14 is thinned by disease, with the suture holes 60, 62. Preferably, non-absorbable nylon sutures are used in the suture holes 60, 62 to secure the plate 40, such as 8-O nylon or polypropylene sutures.

The drainage tube 46 tunnels out through the sclera 14 and the cornea 16 beneath Tenon's capsule 70 and in through an incision 72 in the region of the limbus 22 such that the inflow end 52 of the tube 46 extends into the anterior chamber 30 of the eye 12. A suture is typically used inside the tube as a stent to maintain stiffness during insertion. A dissolvable holding suture may be used to secure the tube 46 to the exterior of the sclera. A bend forms in the tube 46 just before entering the incision 72. The exposed portion of the drainage tube 46 is then typically covered with a scleral reinforcing element (not shown), such as a connective tissue graft, i.e., a sclera graft, dura mater graft, fascia lata graft, or a graft formed from other biocompatible materials.

A large drainage bleb 74 eventually surrounds the plate 40 and lifts the layer of Tenon's capsule 70 above the sclera 14. The plate 40 acts as a permanent bleb-controlling stent to inhibit the tendency of the body to heal itself which would eliminate the bleb. Fibrous rivets of scar tissue 76 form on both sides of the plate 40, causing a low bleb. The tube 46 and plate 40 are designed to initially restrict fluid flow after implant, but gradually permit flow. No valve is required.

One advantage of the presently disclosed glaucoma shunt is a reduced bleb size, both in footprint and height. Several structural features incorporated into the glaucoma shunt 10 of FIGS. 3 and 4 bring about a smaller bleb, and the use of selective areas of cell adhesion, described below, may be used in conjunction. One such feature is a decreased size of the plate 40 combined with more fenestrations 64. Another feature is a reduced height ridge 56 for attaching the outflow end 50 of the drainage tube 46. Furthermore, a variety of novel drainage tube designs may lower complication rate with regard to tube mobility and tube erosion. Each of these features will be described below.

It should be understood that the diverse modifications to prior glaucoma shunts described herein may be independently implemented or combined with each other or other features. For instance, a smaller plate in conjunction with texturing on the plate and/or drainage tube may be utilized, or a lower plate ridge with a modified drainage tube. Moreover, known solutions such as flow restrictors or valves may be added. In short, it should be understood that various combinations of the solutions disclosed herein are within the scope of the invention.

In terms of modifications to the size of the plate 40, a decreased surface area in comparison with earlier plates is believed to reduce complications post surgery as well as ease implantation. The currently available glaucoma shunts have plates with a surface area of about 350 mm². Commercially available plates have four fenestration holes, which has a proven track record. The overall surface area of the plate could be reduced by increasing the number of fenestrations from the current four.

Certain assumptions can be made with regard to glaucoma shunts in order to predict fluid flow and design a plate for controlled flow management. With reference again to FIGS. 3 and 4, the thickness of the plate 40 is preferably in the range of about 0.5 to 3.0 mm, and in an exemplary embodiment is about 0.94 mm. For the smallest thickness of 0.5 mm, an assumed bleb height is about double that, or 1 mm, though a range of between 0.5-1.0 mm is possible. That assumption stems from examination of images of implanted shunts from Lloyd, M. A., et al., "Intermediate-Term Results of a Randomized Clinical Trial of the 350-Versus the 500 mm² Baerveldt Implant," Opthalmology, August, 1994, 101(8). In accordance with the formula below, the reduction in plate area G will be maximized if the radius of fenestration hole is identical to the bleb height.

With reference to FIG. 1, the flow of aqueous fluid around a functioning implanted shunt first emerges from the outflow end 50 of the drainage tube 46 on the outer face 42 of the plate 40. Aqueous fluid distributes within any spaces defined within the bleb 74 around the plate 40, including through fenestrations 64 to the inner face. Gradually, aqueous diffuses through the surrounding tissue at a rate that is determined by the surface area of that tissue exposed to fluid. Consequently, the flow rate may be managed by designing a shunt to optimize the surface area of tissue exposed to fluid. It has been recognized that each plug of tissue that grows through the fenestrations 64 presents a cylindrical surface into which fluid also diffuses. Therefore, adding fenestrations 64 supplies that cylindrical tissue surface area in lieu of a circular area of tissue that would otherwise be exposed above the plate. That increase in tissue surface area can then be accounted for when designing the overall plate dimensions. The following equation represents the reduction in plate size G based on these observations:

$$G = M(\pi R^2) - M(2\pi RB)$$

where:
M=number of fenestration holes,
R=radius of fenestration holes, and
B=bleb height.

Furthermore, a new effective plate surface area $A_{eff}$ is equal to the reference surface area A (e.g., 350 mm²) plus G (which is negative):

$$A_{eff} = A + G$$

Another term that is useful is the ratio of the area of the fenestration holes divided by $A_{eff}$:

$$F = (M\pi R^2)/A_{eff}$$

To assure stability of the plate the ratio F should not be too high, and preferably is lower than 0.8.

Finally, by setting the radius of the fenestration holes R to the bleb height B, which, again, maximizes the reduction in plate size G, the equation may be simplified to derive an optimum number of holes M for a given plate size reduction G, as follows:

$$M = |G/\pi B^2|$$

Several exemplary configurations are presented in the tables below.

TABLE I-A

| Reduction in plate size, tissue reference surface area = 350 mm² | | | | |
|---|---|---|---|---|
| Plate thickness (mm) | 0.5 | 0.5 | 1 | 1 |
| Bleb height (mm) | 1 | 1 | 2 | 2 |
| Hole radius (mm) | 1 | 1 | 2 | 2 |
| A (mm²) | 350 | 350 | 350 | 350 |
| G (mm²) | −101 | −157 | −101 | −151 |
| $A_{eff}$ (mm²) | 249 | 193 | 249 | 199 |
| M | 32 | 50 | 8 | 12 |
| F | 0.40 | 0.81 | 0.4 | 0.76 |

These values are considered practical alternatives to reduce the overall plate size. Other values may be obtained by assuming a reference plate surface area A of between 200-400 mm², as follows:

TABLE I-B

| Reduction in plate size, tissue reference surface area = 250 mm² | | | | |
|---|---|---|---|---|
| Plate thickness (mm) | 0.5 | 0.5 | 1 | 1 |
| Bleb height (mm) | 1 | 1 | 2 | 2 |
| Hole radius (mm) | 1 | 1 | 2 | 2 |
| A (mm²) | 250 | 250 | 250 | 250 |
| G (mm²) | −63 | −110 | −101 | −113 |
| $A_{eff}$ (mm²) | 187 | 140 | 149 | 137 |
| M | 20 | 35 | 8 | 9 |
| F | 0.34 | 0.79 | 0.67 | 0.83 |

TABLE I-C

| Reduction in plate size, tissue reference surface area = 400 mm² | | | | |
|---|---|---|---|---|
| Plate thickness (mm) | 0.5 | 0.5 | 1 | 1 |
| Bleb height (mm) | 1 | 1 | 2 | 2 |
| Hole radius (mm) | 1 | 1 | 2 | 2 |
| A (mm²) | 400 | 400 | 400 | 400 |
| G (mm²) | −101 | −173 | −101 | −151 |
| $A_{eff}$ (mm²) | 299 | 227 | 299 | 249 |
| M | 32 | 55 | 8 | 12 |
| F | 0.34 | 0.76 | 0.34 | 0.61 |

Another way to reduce the size/height of the bleb is to reduce the size of the ridge 56. Since the ridge 56 acts as an anchor for the drainage tube 46, reducing the size of the tube enables a reduction in the height of the ridge 56.

The drainage tube 46 is preferably about 5 mm to 35 mm in length, formed of SILASTIC®, Medical Grade RX-50, also available from Dow Corning Corporation or Nusil Corp. of Santa Barbara. In addition to Silicone, Teflon or polyurethane are also materials that may be suitable for the tube 46. The tube 46 may be extremely thin so as to function as a temporary flow restrictor to stem the loss of aqueous fluid prior to proper formation of a bleb.

In determining the minimum size of the drainage tube 46, the wall thickness should strike a balance between stiffness and flexibility. A minimum stiffness is required to insert the inflow end of the tube into the eye, unless a suture stent is used, while at the same time the tube must be flexible to make an angle from the sclera into the eye without kinking. Also, certain fluid flow characteristics must be considered. The total facility (conductance) of aqueous flow in the human eye is considered to be 0.3 µl/minute per mmHg (as found in Adler's physiology of the eye p. 257). The desired fluid resistance is the inverse of the facility, or 3.33 mmHg per µl/minute. This value could also be obtained from the pressure difference between the eye chamber (normal value is 15-16 mmHg) and the epi sclera (9-10 mmHg), divided by the aqueous flow ranging from 1.5 to 4.0 µl/minute.

Preferably, an elastomeric drainage tube having an open lumen and a length sufficient to extend into the anterior chamber of the eye, should have a lumen diameter of less than 100 microns (radius of less than 50 microns). More preferably, the inner tube lumen radius should be less than 50 microns and greater than or equal to a magnitude determined by the Hagen-Poiseuille equation:

$$r = (8\eta L/\pi R)^{0.25}$$

where:
average aqueous resistance R=3.333 mmHg/microliter/minute,
1 mmHg=133.3 Pa (kgm/s$^2$),
1 microliter/minute=$1.667 \times 10^{-11}$ m$^3$/s,
L=length of tube (mm),
Average aqueous resistance R=$2.666 \times 10^{13}$ kg/sm$^2$, and dynamic viscosity $\eta$=$7.50 \times 10^{-4}$ kg/sm.

The following table shows parameters for four different tube configurations:

TABLE II

Drainage tube radius vs. length

| Length (mm) | Radius (micrometer) | max. velocity (m/s) | Reynolds No. |
|---|---|---|---|
| 30 | 38.3 | 0.013 | 521 |
| 25 | 36.6 | 0.014 | 476 |
| 20 | 34.6 | 0.016 | 426 |
| 15 | 32.2 | 0.018 | 369 |

The edges of the plate 40 are desirably radiused, tapered and blended so as to facilitate insertion. Additionally, the rounded edge of the plate 40 discourages unwanted growth of scar tissue on the plate 40 which may lock the plate 40 into an undesirable position. The rounded edge of the plate 40 also presents a smooth surface from which scar tissue preferably slides off and is therefore unable to completely anchor onto the plate 40.

FIGS. 5A-5D show outer face plan views of alternative glaucoma shunts 100, 200, 300, 400 having selective cell adhesion regions 120, 220, 320, 420 having increased propensity for cell adhesion, such as texturing, alternating with surface regions 122, 222, 322, 422 that have relatively lower propensity for cell adhesion. The term "regions of increased cell adhesion" means regions on surfaces of the plates of the glaucoma shunts 100, 200, 300, 400 that have greater tendency to adhere to surrounding tissue than other regions. Typically, that means regions with texturing or a chemical coating adjacent to smooth untreated regions. Texturing a polymeric surface such as silicone enhances fibroblast and epithelial cell adhesion, and the same response may be created with surface treatments. However, the benefits of providing selective regions of increased cell adhesion does not depend on a binary construction, and the terms increased and decreased cell adhesion may be relative, with regions of lesser cell adhesion actually inducing some cell adhesion. The idea is to promote greater cellular and tissue attachment in preselected locations to improve the performance of the implant. Specifically, glaucoma shunts disclosed herein may be engineered such that regions of increased cell adhesion promote cellular attachment/tissue adhesion in desired locations only, while other regions have lessened or no tissue adhesion. Benefits of such a structure and attendant tissue response include more controlled intraocular pressure (IOP) reduction, a smaller bleb, and better implant fixation. Selective texturing is believed to prevent and/or reduce micro motion at the implant-tissue interface which in turn reduces the thickness of the bleb, prevents extrusion of the shunt, and may even reduce the need for human pericardium or sclera allograft.

It should be understood that the outer face plan views of glaucoma shunts 100, 200, 300, 400 shown in FIGS. 5A-5D are representative of either or both the inner and outer faces thereof. That is, the selective cell adhesion regions may be provided on only the inner face, only the outer face, or both. Furthermore, numerous patterns of the cell adhesion regions are contemplated, and if they are provided on both inner and outer faces of the shunts they may be identical or different. For instance, a desired pattern of cell adhesion regions for the outer face may not be optimal for the inner face. Finally, regions of increased cell adhesion may be provided only on the periphery of the shunts or only on the drainage tube, or either location in conjunction with other areas. Of course, numerous other configurations of alternating cell adhesion regions and surface regions are possible, the illustrated versions being shown only for example.

Figure 5A:
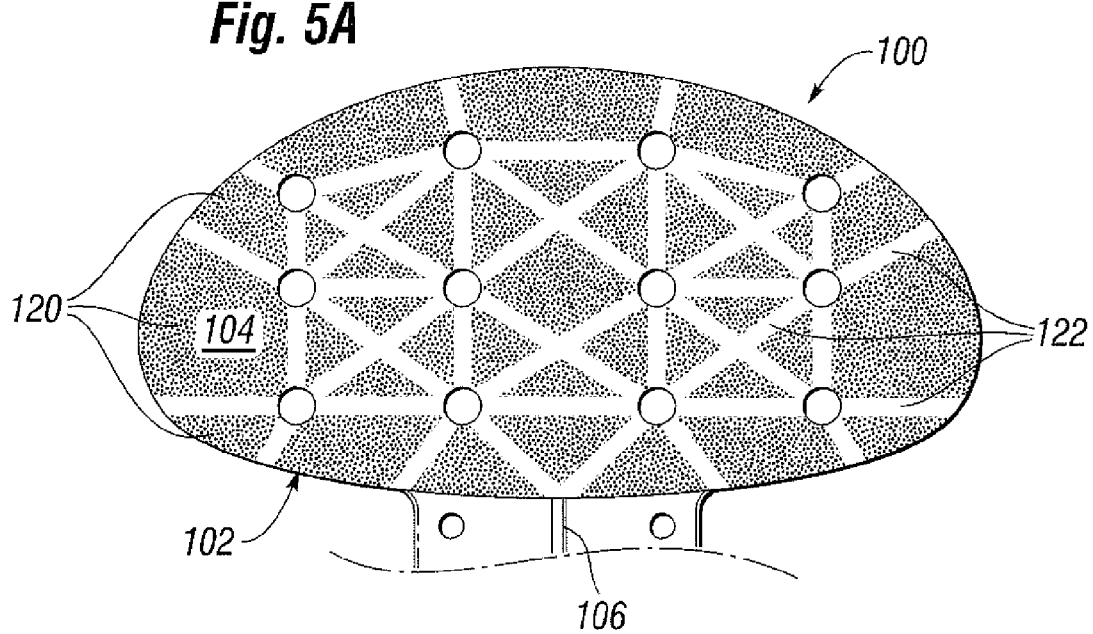
FIGS. 5A-5D are outer face plan views of alternative glaucoma shunts disclosed herein having regions of increased cell adhesion, e.g., texturing, alternating with smooth surface regions.

With reference to FIG. 5A, the glaucoma shunt 100 comprises a generally oval-shaped pliable plate 102 having oppositely disposed convex outer 104 and concave inner (not shown) faces. As before, the curvature of the plate 102 desirably conforms to the sclera 14 and connects to a discharge or drainage tube 106 with a length sufficient to extend into the anterior chamber 30 of the eye 12. Certain other elements are not numbered or discussed and may be the same as in the earlier shunt 40 of FIGS. 3 and 4, but are only shown as exemplary and may be omitted. For instance, the peripheral ridge may be omitted in favor of a constant thickness plate 102 at the peripheral edge.

The glaucoma shunt 100 includes an exemplary fenestration pattern with twelve fenestrations 110 distributed generally evenly across the plate 102. As before, the fenestrations 110 comprise round holes extending completely through the plate 102. In the illustrated embodiment, the twelve fenestrations 110 are distributed in three rows of four, with the upper row extending in a slight arc to mirror the curved contour of the nearest outer edge of the plate 102. Of course, the number and arrangement of fenestrations 110 may be altered, though a generally even distribution across the plate 102 is believed to best spread out the flow of fluid therethrough and therefore influence formation of an even height bleb and consistent fixation across the plate.

As seen in FIG. 5A, the outer face 104 features select cell adhesion regions 120 of increased cell adhesion alternating with surface regions of reduced cell adhesion 122. In the illustrated embodiment, and for purpose of discussion, the cell adhesion regions 120 comprise texturing, preferably microtexturing. The selective pattern that resembles leaf veins forms interconnected channels that isolate at least one of the cell adhesion regions 120 from the others. That is, the surface regions 122 of reduced cell adhesion define a plurality of channels for fluid flow. The channels desirably connect adjacent fenestrations 110, and more preferably connect each group of four fenestrations 110 to each other with a rectangular pattern of channels around the periphery and channels that extend across diagonally. The aim of such channels is to conduct aqueous fluid across and from inner face to outer face 104 in a highly distributed manner. Also, a V-shaped channel leading from the outflow end of a drainage tube 106 helps initially distribute fluid laterally. Conversely, if the entire outer face 104 were textured, then much less fluid flow across the face would occur. In the illustrated embodiment, fluid can flow between fenestrations 110 and from one face of the plate 102 to the other, thus equilibrating fluid pressure more effectively.

Microtexturing or a surface with increased cell adhesion may also be provided on the exterior of the drainage tube 106. Such microtexturing helps the tube 106 adhere to the pathway through the sclera, and thus helps prevent undesired movement therein which may prevent extrusion of the tube.

Figure 5B:
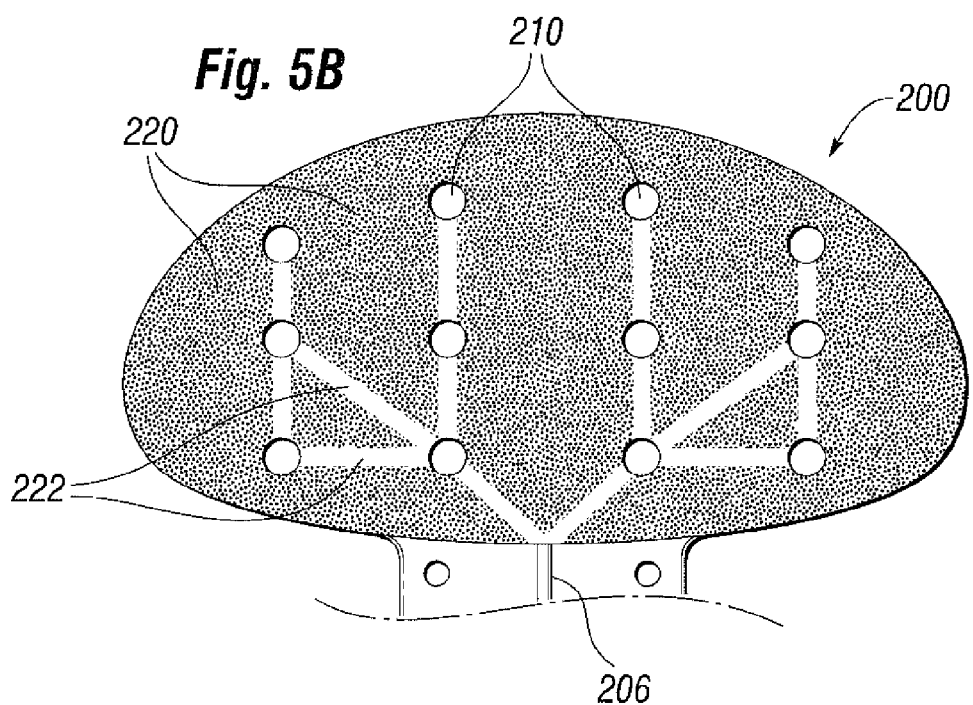

The glaucoma shunt 200 shown in FIG. 5B is similarly constructed as the version in FIG. 5A, with select cell adhesion regions 220 of increased cell adhesion alternating with surface regions 222 of reduced cell adhesion in a leaf-vein-like pattern. In this embodiment, however, the cell adhesion regions 220 are increased to reduce the number of flow channels formed therebetween. A V-shaped channel leading from the outflow end of a drainage tube 206 helps initially distribute fluid laterally, and there are lateral channels across the lower row of fenestrations 210, but otherwise the plate 202 only features vertical channels (or those parallel with the direction of the outflow end of the drainage tube 206).

Figure 5C:
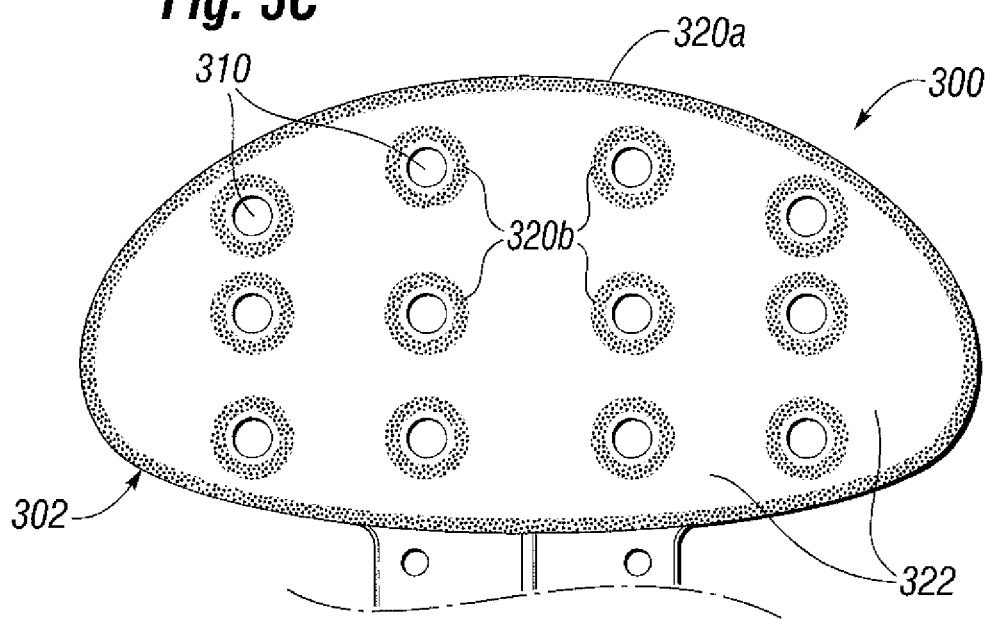

The glaucoma shunt 300 shown in FIG. 5C also has select cell adhesion regions 320 of increased cell adhesion alternating with surface regions 322 of reduced cell adhesion. In this embodiment, a peripheral cell adhesion region 320a is provided around the peripheral edge of the plate 302 and circular regions 320b surround each fenestration 310. The circular regions 320b surrounding each fenestration 310 are desirably spaced from the fenestration by between about 1-5 mm. The shunt 300 may have just the peripheral cell adhesion region 320a, or just the circular regions 320b, or only some of the latter, etc. Many variations are contemplated.

Figure 5D:
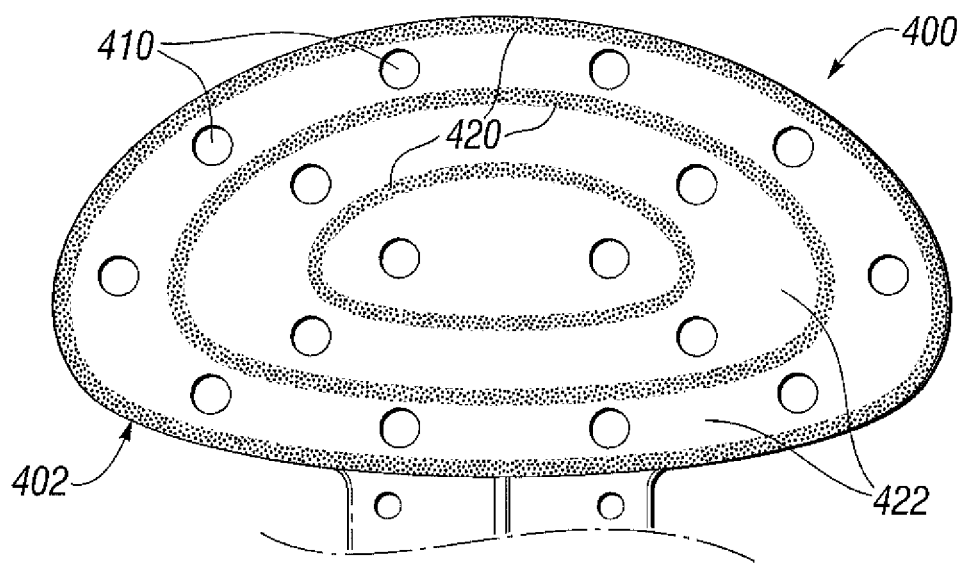

FIG. 5D illustrates a glaucoma shunt 400 with concentric oval-shaped cell adhesion regions 420 of increased cell adhesion alternating with oval-shaped surface regions 422 of reduced cell adhesion. A plurality of fenestrations 410 are provided within the surface regions 422, or alternatively they could overlap the cell adhesion regions 420. Breaks in the oval-shaped cell adhesion regions 420 may be provided to permit fluid flow between the channels defined by the surface regions 422.

The term "microtexturing" preferably refers to elements protruding outward to peaks (or etched down into the surface) from whatever surface they are on and separated by valleys, wherein the average peak-to-valley depth normal to the outer face is between about 0.5-10 microns. Furthermore, texturing that is uniform and has dimensions smaller than rounded cells (typically >15 microns) has better outcomes in in vitro and in vivo models. It is believed that cells agglomerate and adhere more reliably on uniform, regular structures with sharp corners with smaller dimensions, and the resulting fibrous encapsulation (i.e., bleb formation thickness) will be much less. That is, texturing with sharp corners promotes focal adhesions. Preferably, the texturing includes grooves, ridges, wells or pillars. For example, for grooves, the pitch could be 4 microns (2 micron groove, 2 micron ridge) and 0.5 micron depth.

More particularly, the texturing may comprise a plurality of periodically-spaced protrusions, each protrusion having a smooth distal face and at least one sharp corner edge configured to engage at least one cell. The protrusions extend from the surface portion (or up from etched depressions) by an amount that is between about 0.5 micron and about 10 microns, preferably between 0.5 micron and about 2 microns, and more preferably between 0.5-1.0 microns. The sharp corner edges preferably have a radius that is less than about 200 nanometers, more preferably less than 100 nanometers, and even more preferably less than 20 nanometers. The smooth distal faces of the protrusions generally have an RA surface roughness that is less than about 200 nanometers, preferably less than 50 nanometers, even more preferably less than about 20 nanometers. The roughness of the other surfaces of the textured surface may be greater than that of the smooth distal faces.

In one embodiment, the texturing protrusions comprise a plurality of pillars and the smooth distal faces are circular; however, other shapes and configurations of the protrusions are possible (e.g., smooth distal faces may be rectangular, oval, or some other shape; the protrusions may be configured to form concentric rings, as discussed below herein). Each protrusion may further comprise a side wall, such that the sharp corner edge 134 is formed along an intersection of the side wall and the smooth distal face. The sharp corner edges are desirably perpendicular to the smooth distal face, though the two surfaces may form an angle that is between about 60-120° so as to form more of a cone or inverted cone. Further details of exemplary texturing may be seen in the discussion of protrusions on intraocular lenses described in U.S. Patent Publication 2008/0077238 to Deacon, et al., filed Sep. 21, 2006, and expressly incorporated by reference herein.

To form the selective texturing or microtexturing the most straight-forward method is to reverse texture the mold. The mold can be textured by induced texturing, or ion bombardment sputtering techniques, in which a seeding material acts like a mask on the base mold (such as titanium) allowing for selective erosion. The silicone plate 102 could also be textured by embossing. That is, the silicone plate 102 could be placed between 2 microtextured plates or 1 microtextured plate and 1 non-textured plate in a Carver press for a given time and temperature. Alternatively, etching may be used to form the selective texturing or microtexturing. Still further, the texturing could be achieved by adding coatings such as chemical coatings. Potential coatings include: polyethylene glycol (PEG), heparin, nano-coatings of titanium selectively sputter-coated, silicone oxide, and silicone oxide with polyethylene glycol. For instance, a coating of titanium may be selectively sputter-coated, or silicone oxide or silicone oxide with poly(ethylene oxide) with the correct dimension may be "grown" on the silicone plate. To be clear, like the microtexturing, the coating may be on both surfaces, one surface, partial surface (patterns), with or without microtexturing.

Another problem area with glaucoma shunt implant is irritation to the eye from the physical presence of the implant, or even erosion of surrounding tissue from frictional movement of the structure, in particular the drainage tube. Because the tube is a cylinder, it may roll on the sclera and irritate or even erode the sclera or the encompassing conjunctiva.

Figure 6:
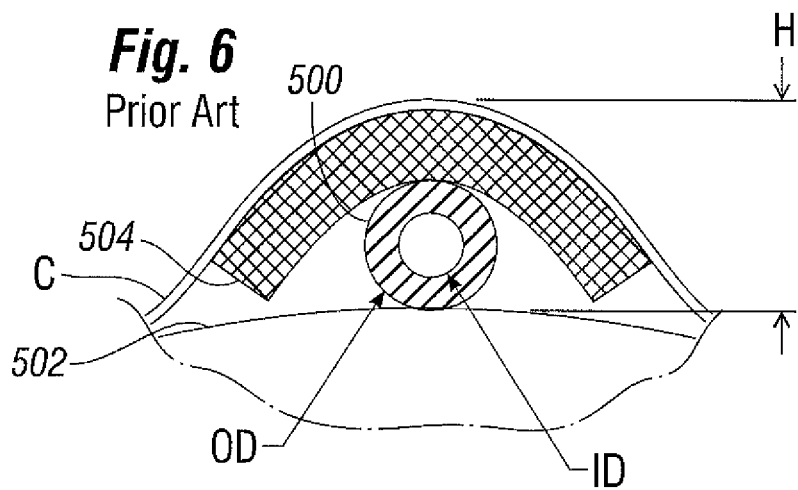
FIG. 6 is a cross-sectional view of a drainage tube used with glaucoma shunts of the prior art.

FIG. 6 shows the cross-section of a typical drainage tube 500 fixated on the sclera 502. Often, a section of donor tissue or graft 504 is secured over the tube 500 and under the conjunctiva C. The graft 504 helps distribute contact forces along the generatrix of the tube 500, but movement from rubbing the eye sometimes erodes the sclera 502. Furthermore, the overall height H of the structure presents an irritation to the patient. One solution is to reduce the diameter of the tube 500, as mentioned above.

Figure 7:
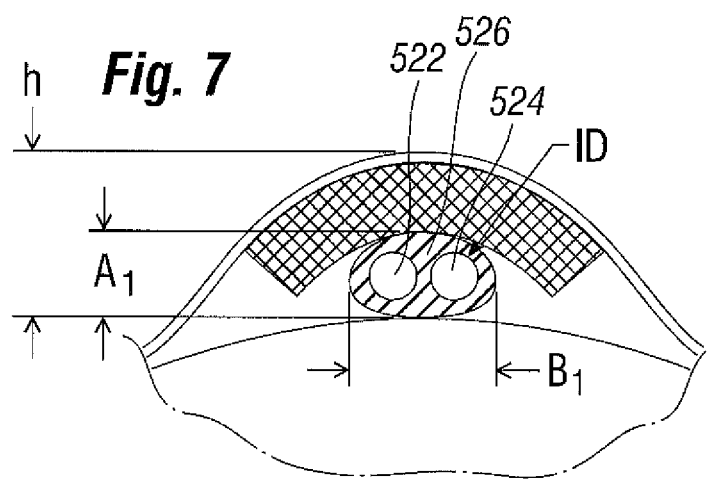
FIGS. 7 and 8 are cross-sectional views of exemplary drainage tubes for use with various glaucoma shunts disclosed herein.

Furthermore, the profile of the tube may be modified to retain the fluid flow characteristics but lower its height. For instance, FIG. 7 shows an oval-shaped drainage tube 520 having a minor dimension $A_1$ and a major dimension $B_1$. Two lumens 522, 524 separated by a bridge 526 transmit the same volume of fluid as with a single circular lumen, but the overall height h of the structure is reduced. Several benefits accrue. For one, the lessened height h presents a smaller physical bulge in the eye and consequent reduction in patient discomfort. Secondly, the flatter profile reduces the likelihood of the tube 520 rolling upon the patient rubbing the spot on the eye. Finally, the bridge 526 provides a structural stiffener to help prevent kinking of the tube as it bends into the inner chamber of the eye. Indeed, in an alternative, a single oval-shaped lumen may be used as long as the structure resists kinking. In one embodiment, the minor dimension $A_1$ is 0.4 mm, the major dimension $B_1$ is 0.7 mm, and the diameter of the two identical lumens 522, 524 is 0.2 mm.

Figure 8:
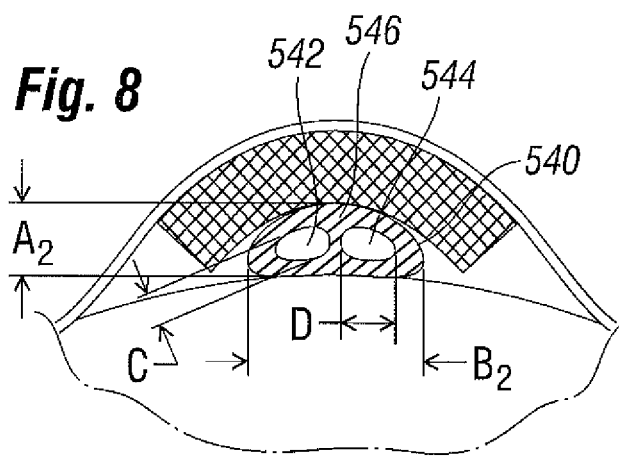

FIG. 8 depicts an alternative oval-shaped drainage tube 540 having a minor dimension $A_2$ and a major dimension $B_2$. As before, two lumens 542, 544 separated by a bridge 546 transmit the same volume of fluid as with a single circular lumen, but again the overall height h of the structure is reduced. The oval shape is modified so that the lateral edges are even further contoured to more comfortably fit inside the graft and conjunctiva. This contouring further reduces patient discomfort and the likelihood of movement of the tube. In one embodiment, the minor dimension $A_2$ is 0.35 mm, the major dimension $B_2$ is 0.8 mm, the height C of the two identical lumens 522, 524 is 0.15 mm and the width D of the two lumens is 0.25 mm.

Figure 9:
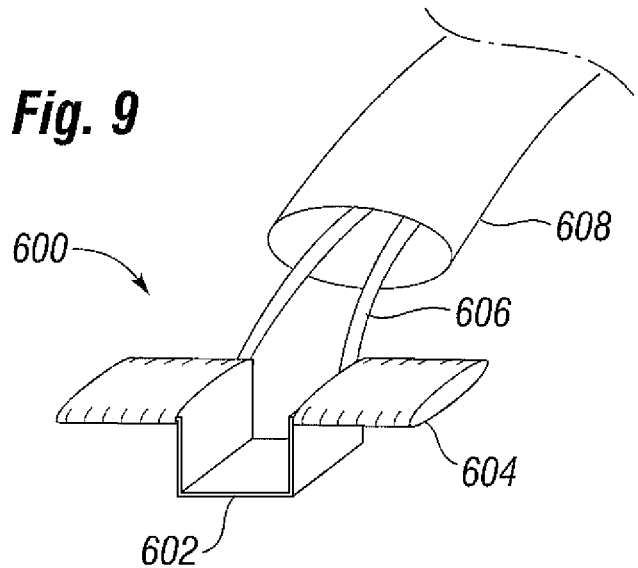
FIG. 9 is a perspective view of a tool that may be used to create a scleral groove for receiving glaucoma shunt drainage tubes.
Figure 10:
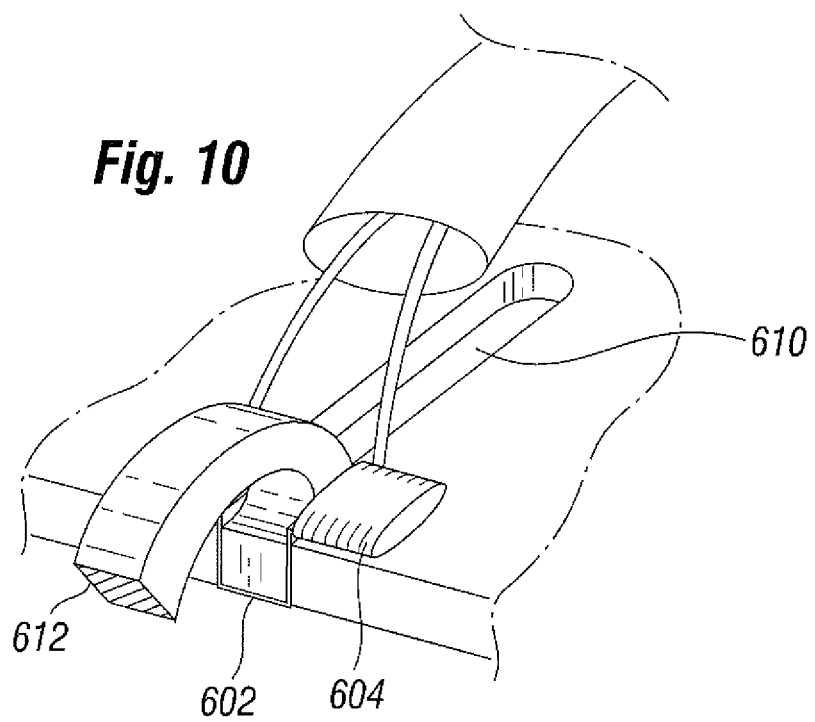
FIG. 10 is a perspective view of use of the tool of FIG. 9.

To further prevent tube movement, a groove may be formed in the sclera to receive the tube. FIGS. 9 and 10 illustrate an exemplary tool 600 for forming such a groove. The tool 600 includes a blade 602 having a two-dimensional leading edge, in this case rectangular, though other shapes such as V-shaped or semicircular may be suitable. Two wings 604 flank the blade 602, and the tool further includes a pair of manipulators 606 connected to a handle 608.

FIG. 10 shows the tool 600 in the process of forming a trough or groove 610 in the sclera by removing a section of tissue 612. The depth of the blade 602 is controlled by the relative position of the wings 604. Desirably, the wings 604 are rounded and formed of a soft or lubricious material to reduce any incident damage to the sclera.

Figure 11A:
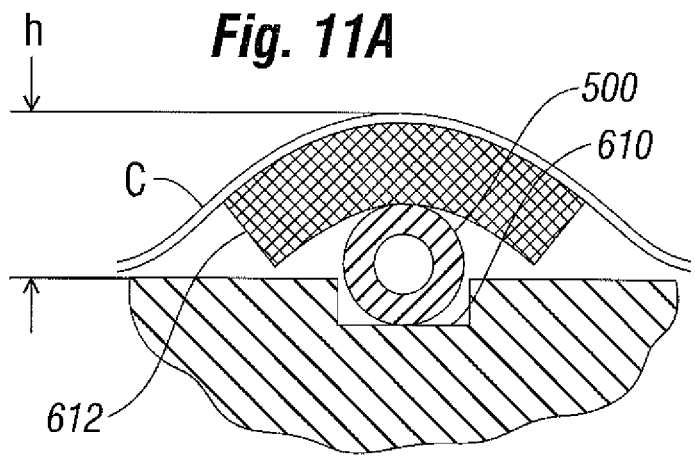
FIGS. 11A-11C are cross-sectional views of exemplary scleral grooves with the drainage tubes of FIGS. 6-8, respectively, positioned therein and a flap of tissue or other material thereover to fix the tubes within the grooves.
Figure 11B:
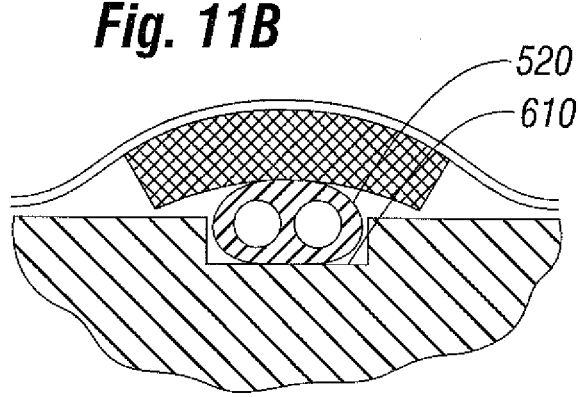
Figure 11C:
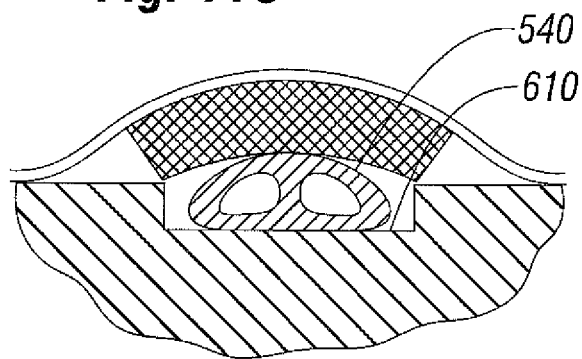

Once the groove 610 is formed, the drainage tube may be placed therein and covered with the aforementioned tissue graft and conjunctiva C. For instance, a conventional drainage tube 500 is seen in a groove 610 in FIG. 11A. The strip of sclera tissue 612 cut during the formation of the groove 610 may be used for the tissue graft. The overall height h is reduced from the conventional arrangement seen in FIG. 6. FIGS. 11B and 11C show placement of the modified tubes 520 and 540 in grooves 610, which even further reduces the overall height of the assembly. It should be noted that the use of a groove, especially with a contoured tube profile as in FIGS. 11B and 11C, may obviate the need for a graft over the top of the tube as the tube remains stationary with a relatively low profile, reducing tube movement as well as the irritation sometimes felt with larger profiles and the subsequent rubbing and tube movement.

In addition to aspects of glaucoma shunts that manage flow after a predetermined time, the present application also presents a solution for the initial period before adequate formation of the bleb. That is, for a period of between 1-2 months while the scar tissue heals around the implant, aqueous should not flow freely through the drainage tube for risk of inducing a harmful low IOP. Consequently, the present application contemplates a flow restrictor for use in non-valved glaucoma drainage devices in order to control aqueous flow directly after implantation, but that also immediately lowers the intraocular pressure (IOP).

The flow restrictors described herein are positioned in the drainage tube between the scleral plate and the bend in the drainage tube which enters an incision toward the eye chamber. The flow restrictor may be held in position by an absorbable suture tied around the tube during the first weeks of the post-operative period until the bleb around the plate is formed, or by an internal feature in the tube as shown. Early aqueous flow is controlled by the flow restrictor until the flow restrictor dissolves, after which the bleb controls the aqueous flow. The presence of the tubular flow restrictor within the drainage tube also helps reduce instances of tube fracture which may occur if the surgeon applies a suture ligature. Surgeons want to be sure that there is no aqueous flow before bleb formation and sometimes they applied too much force on the suture thereby breaking the tube. However, if the suture is applied around the tube where the flow restrictor sits, then the chance for tube fracture will be significantly reduced.

Preferably, flow restrictors described herein have an outer diameter that fits the inner tube diameter of the glaucoma shunt (e.g., 0.3 mm for the current Baerveldt shunt). The flow restrictors are also desirably placed an appropriate distance between the plate and the bend in the drainage tube that descends into the eye (typically a length between about 1-4 mm).

The most straight forward geometry for the flow restrictor is based on a tube, though other geometrical configurations are possible (also multiple holes) as long as the desired facility is obtained to flow aqueous so that the desired IOP level is reached.

Figure 12A:
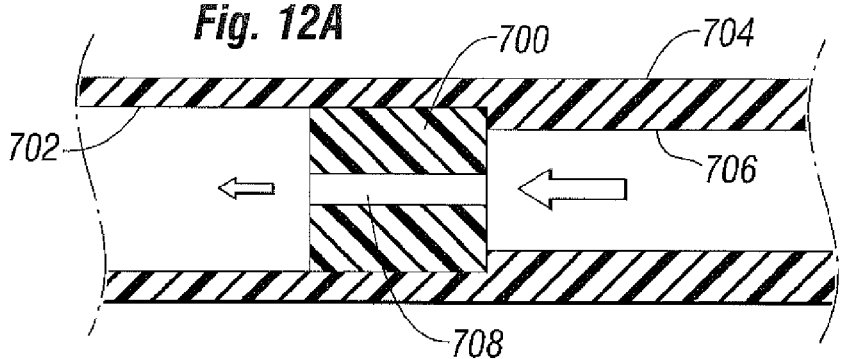
FIGS. 12A and 12B are longitudinal sectional views of an exemplary flow restrictor within a shunt drainage tube.
Figure 12B:
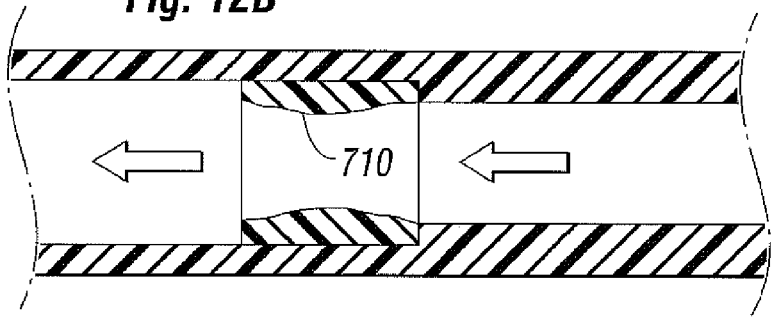
Figure 13A:
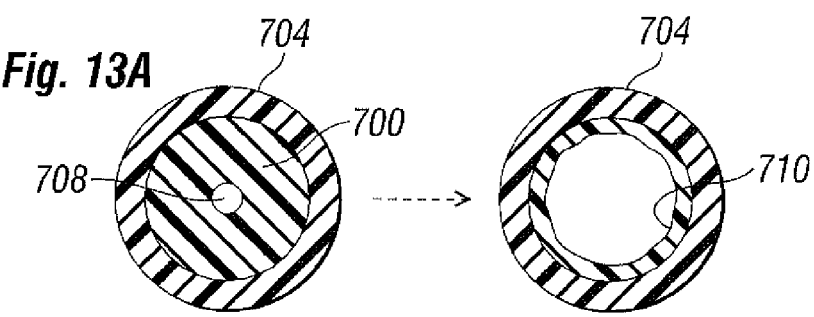
FIGS. 13A-13C are cross-sectional views of alternative flow restrictors within shunt drainage tubes.

FIGS. 12A and 12B are longitudinal sectional views of an exemplary flow restrictor 700 positioned within a first lumen 702 of a shunt drainage tube 704. The restrictor 700 has a tubular configuration with a cylindrical exterior shape that fits against a shoulder between the first lumen 702 and a second, smaller lumen 706 in the tube 704. The step between the two lumens prevents the flow restrictor 700 from entering the chamber of the eye. The restrictor 700 defines a relatively small throughbore 708 that initially permits a small flow of aqueous therethrough, thus relieving some of the built up IOP. Over time, as indicated in FIG. 12B and FIG. 13A, the material of the flow restrictor 700 dissolves in the aqueous and a larger throughbore 710 forms. The flow gradually increases to a magnitude at which the downstream bleb functions as the pressure regulator.

The flow restrictor 70 could be made of existing available resorbable suture material. A hole of 0.02 mm in a length of suture having a 0.3 mm outer diameter could be laser manufactured or extruded. After bleb formation the suture holding the flow restrictor could be released, and the flow restrictor will flow towards the bleb.

In designing a cylindrical flow restrictor, certain fluid flow characteristics must be considered. The total facility (conductance) of aqueous flow in the human eye is considered to be 0.3 µl/minute per mmHg. The desired resistance for the flow restrictor is the inverse of the facility, or 3.33 mmHg per µl/minute. This value could also be obtained from the pressure difference between the eye chamber (normal value is 15-16 mmHg) and the epi sclera (9-10 mmHg), divided by the aqueous flow ranging from 1.5 to 4.0 µl/minute.

From the law of Hagen-Poiseuille for a laminar flow through a cylindrical tube of length L, inner radius r, the resistance equals $8\eta L/\pi r^4$, where $\eta$ is the dynamic viscosity with value of $7.50\times10^{-4}$ Kg/ms for aqueous humor at 37° C.

For one length the radius range is only up to about 5 µm which is close to manufacturing tolerances. The typical geometry of a cylindrical two millimeters long flow restrictor is an outer diameter almost equal to inner diameter of the tube of the glaucoma shunt involved (0.3 mm is applicable for the Baerveldt shunt), and an inner diameter of 0.02 mm.

In the table below the flow conditions are checked by calculating Reynolds number for the typical resistance values of 3.33 mmHg per µl/minute.

TABLE III

Flow restrictor throughbore radius vs. length

| Length (mm) | Radius (micrometer) | max. velocity (m/s) | Reynolds No. |
|---|---|---|---|
| 4 | 23.1 | 0.036 | 190 |
| 3 | 21.5 | 0.041 | 165 |
| 2 | 19.5 | 0.050 | 135 |
| 1 | 16.4 | 0.071 | 95 |

The flow is thus very laminar, validating use of the law of Hagen-Poiseuille as applied to calculate the dimensions of the flow restrictor.

Figure 13B:
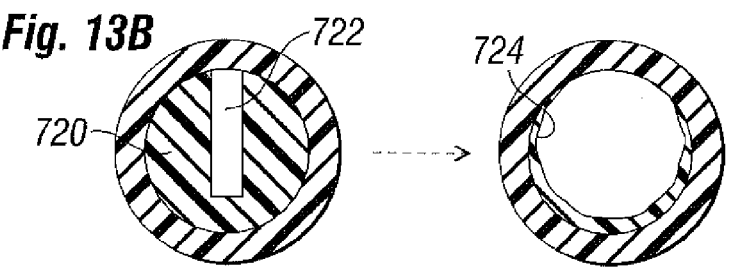
Figure 13C:
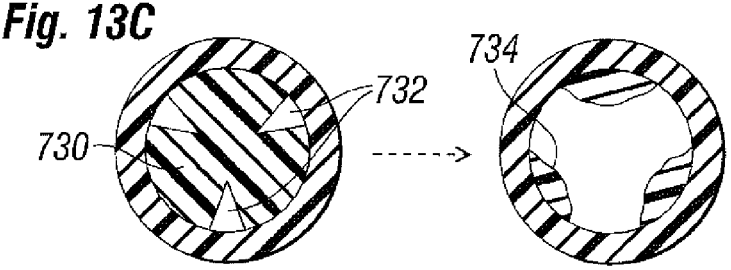

FIGS. 13B-13C are cross-sectional views of alternative flow restrictors within shunt drainage tubes. FIG. 13B shows a cylindrical flow restrictor 720 having a keyhole-shaped throughbore 722. The resulting eroded shape 724 is shown to the right. Any non-symmetric or otherwise non-circular throughbore could be used if it adequately prevented full flow for the desired time frame, after which it no longer presented an appreciable drag on flow. For instance, FIG. 13C shows a flow restrictor 730 with three spaced triangular notches 732 on its periphery. Aqueous eventually dissolves the material to leave remnants 734, or none at all if the flow washes them downstream.

Figure 14A:
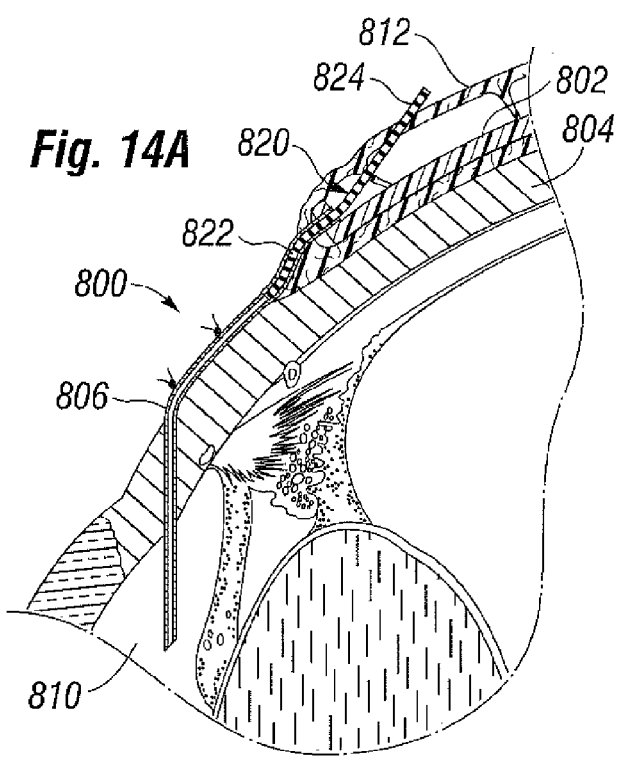
FIGS. 14A and 14B are cross-sectional view of the human eye showing an alternative flow restrictor within a glaucoma shunt drainage tube.
Figure 14B:
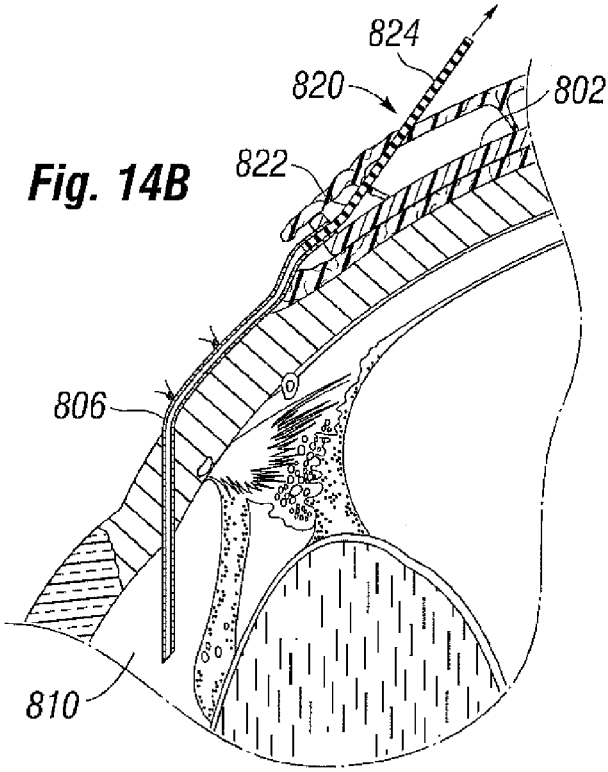

In addition to resorbable flow restrictors as described above, the present application contemplates flow restrictors that can be moved to control the pressure gradient through the drainage tube, thus more accurately regulating the intraocular pressure (IOP). FIGS. 14A and 14B are cross-sectional view of the human eye in which a glaucoma shunt 800 constructed in accordance with the present application is positioned. As described above, a curved pliable plate 802, also referred to as a pliable seton, conforms to the sclera 804 and connects to a discharge or drainage tube 806 that extends into the anterior chamber 810 of the eye. A drainage bleb 812 eventually surrounds the plate 802.

The tube 806 and plate 802 are designed to initially restrict fluid flow after implant, but gradually permit flow. This is done using a movable flow restrictor 820 that extends into a lumen of the drainage tube 806. The flow restrictor 820 comprises an elongated thin filament, tube or flexible rod that desirably conforms closely to the inner diameter of the drainage tube 806, permitting some flow but substantially occluding maximum flow therethrough. The length of the flow restrictor 820 is such that a distal portion 822 extends a predetermined distance into the tube 806 and a proximal portion 824 projects upward through the bleb 812. In one embodiment, the flow restrictor 820 includes a through lumen or longitudinal flow channel in at least the distal portion 822, but such a channel does not extend completely along the proximal portion 824 so that a flow passage past the bleb 812 is not created. The proximal portion 824 extending past the bleb 812, however, provides a convenient length that can be grabbed and manipulated post-op. Preferably, the proximal portion 824 projects through the covering tissue (conjunctiva, muscular capsule) far enough to be accessible by a surgeon with minimally-invasive surgery.

The configuration of the flow restrictor 820 is such that it modifies the pressure gradient and flow through the drainage tube 806 depending on how much of the length of the flow restrictor is in the tube. For instance, the flow restrictor 820 may comprises a tube thinner than the inner lumen of the drainage tube 806 and having a lumen that permits some flow therethrough. An open side channel or a porous side wall permits lateral flow out of the proximal portion 824 of the flow restrictor 820 that is not within the drainage tube 806, while the distal portion 822 in the drainage tube limits flow. Therefore, the greater the distal portion 822 in the drainage tube, the more flow is limited.

Figure 15A:
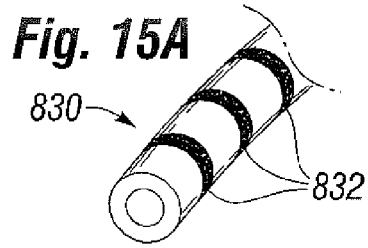
FIGS. 15A-15F are perspective views of several alternative flow restrictors having position indicators thereon.

FIGS. 15A-15F are perspective views of several alternative flow restrictors having position indicators thereon. FIG. 15A shows a constant diameter tube 830 having a series of length indicator bands 832 spaced apart at regular increments along its exterior. The indicator bands 832 may be printed on the tube 830 or formed by physical indents. The bands 832 may be formed by a laser, for example. The bands may be color coded to convey relative position information, but in any event serve to communicate the relative position change of the flow restrictor tube 830 in the drainage tube 806. That is, the flow restrictor tube 830 may be initially placed at a predetermined distance into the drainage tube 806, and then moved farther in or out depending on the measured IOP. If the IOP is too great, more flow is required, and the surgeon will pull the flow restrictor tube 830 farther out of the drainage tube 806 in increments until a desired IOP is attained. In one embodiment, means for visualizing at least the tip of the restrictor within the tube/shunt is provided. For example, a colored tip visible through the clear/opaque tube/shunt may be utilized, such as fluorescent material when seen under blue or violet light.

Figure 15B:
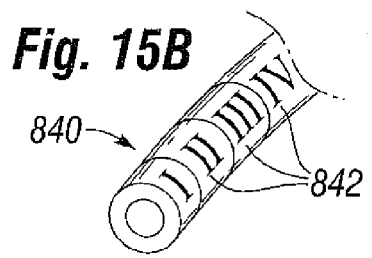
Figure 15C:
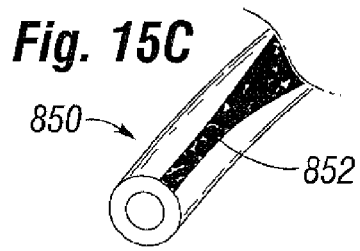

FIGS. 15B and 15C show additional tubular flow restrictors 840, 850 that have exterior markings 842, 852, respectively. The markings 842 provide numerical indicators of the position of the tube 840, while the marking 852 provides a relative position indicator in the form of a gradually increasing slider-like icon. Both tubular flow restrictors 840, 850 function in essentially the same manner as the flow restrictor 830.

Figure 15D:
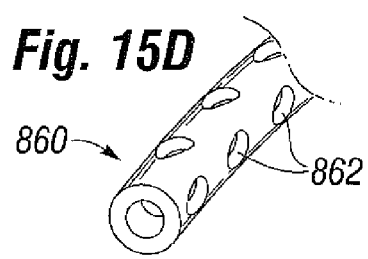

FIG. 15D is slightly different, in that a tubular flow restrictor 860 includes a plurality of side holes or ports 862 along its length. These ports 862 permit flow laterally out of the lumen of the flow restrictor 860 in the proximal portion that is outside of the drainage tube 806.

Figure 15E:
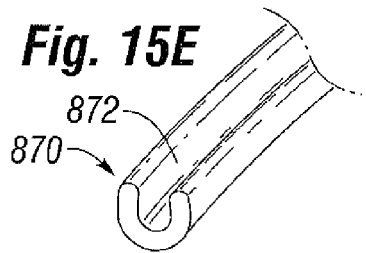

FIG. 15E shows a still further flow restrictor 870 that has a C-shaped cross-section including an open longitudinal channel 872 along its length. As with the side ports, the channel 872 permits flow past the restrictor 870 in the proximal portion that is outside of the drainage tube 806.

Figure 15F:
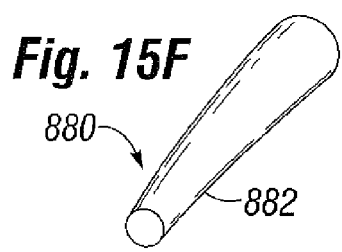

Another controllable flow restrictor solution shown in FIG. 15F is a tapered solid obturator 880 with a narrow distal end 882 that gradually widens in a proximal direction. As the tapered obturator 880 is pulled from within the drainage tube 806 the spacing therebetween gradually increases, thus permitting more flow through the drainage tube.

The various flow restrictors in FIGS. 14-15 are desirably non-dissolvable, but may also be resorbable as desired. In use, the flow restrictor is inserted into the drainage tube prior to implant, most likely during assembly. The surgeon implants the glaucoma shunt and positions the drainage tube in the eye. Based on pressure measurements, the flow restrictor may be adjusted relative to the tube to increase or decrease flow. This may be done in several stages, which is facilitated if the flow restrictor extends a distance beyond the shunt plate. At some point, the surgeon applies a ligating suture to secure the drainage tube, which also secures the flow restrictor therein. One benefit of having the flow restrictor in the drainage tube is to prevent common complications like tube breakage when surgeons apply ligature sutures. That is, a ligature suture around a tube with a flow restrictor inside will be less likely to collapse, kink or cut through the drainage tube. After a period the fixating suture around the tube is removed, or dissolves, which releases constriction on the flow restrictor. The flow restrictor, which in this embodiment is 1-3 mm in length, may then migrate from fluid pressure out of the drainage tube, ending up within the bleb, which is harmless. A short length of polypropylene suture having a through lumen may be suitable for such a flow restrictor.

At the time of implantation it is difficult to measure the intraocular pressure (IOP), which complicates positioning of a movable flow restrictor. One solution is to incorporate a mini pressure sensor onto the glaucoma shunt, with which the IOP can be rapidly measured during implant. For instance, a mini pressure sensor may be provided in a graft that fixes the drainage tube to the outside of the sclera, and have a probe that extends into the tube to measure pressure therein. The flow restrictor may be installed at a presumed proper length within the drainage tube based on an initial estimation of flow volume versus flow restrictor position. The flow restrictor will be set at the default position and then adjusted after equilibrium pressure is established and measured (out for lower pressure, in for greater pressure). NXP, a former division of the Dutch firm Philips, is able to produce mini pressure sensors having dimensions of approximately 80×150× 150 microns that may be suitable. Research into intraocular pressure sensing has been done by Kakaday, et al. in "Advances in Telemetric Continuous Intraocular Pressure Assessment," British Journal of Opthalmology 2009; 93:992-996, and by Mokwa in "Ophthalmic Implants," 2003 IEEE Publication, 980-986, Institute of Materials in Electrical Engineering, RWTH Aachen Univ., Aachen, Germany, the disclosures of which are incorporated by reference herein.

Alternatives for fixating the flow restrictor within the drainage tube include applying an exterior resorbable suture around the tube until it is itself absorbed and stops exerting pressure on the flow restrictor from outside the tube. Or, the absorbable sutures can be assembled during manufacturing. Still further, the force can be applied by a flow restrictor of a polymeric biocompatible memory material that expands when heated to 40° C., e.g. Such an active flow restrictor may be caused to break up or otherwise flow through upon exposure to laser light post-surgery.

Another aspect of the present application that helps prevent endophthalmitis, or an inflammation of the inner eye, is to coat the various implant surfaces with an anti-bacterial coating or agent. For instance, surfaces on the pliable plate 40 or drainage tube 46 shown in FIGS. 1-4 may be covered with an anti-bacterial. In a preferred embodiment, the inner lumen of any of the drainage tubes described herein is coated with an anti-bacterial to ensure exposure of the fluid passing therethrough. Also, the bioresorbable flow restrictors see in FIGS. 12-13 may include an anti-bacterial component which elutes as the device dissolves. Likewise, the movable flow restrictors seen in FIGS. 14-15 are good candidates to have an anti-bacterial coating. Each of these devices has direct contact with the fluid that passes to and from the inner eye, and is thus optimally positioned to effect a reduction in infection during the early post-op stages of the procedure.

The period during which an anti-microbial coating is most beneficial begins immediately post-op and extends at least 2 weeks, and potentially up to 2 months. Eventually, a bleb forms and effectively closes the fluid system from outside bacteria. The amount of time it takes for the bleb to form depends on a number of factors, including the age and health of the patient, and the use of topical medications such as antibiotics or steroids are administered. Preferably, an anti-microbial coating that lasts for about 2 months will provide the intended protection. A coating on a flexible silicone or other polymer shunt conforms to uneven surfaces and reduces irritation as compared to a metallic shunt and may improve adhesion to the surrounding tissues.

A number of suitable anti-bacterial coatings are available, including those that release silver ions (Ag+) or silver nano particles. One supplier of such coatings is Bio-Gate AG of Nurnberg, Germany, which markets antimicrobial additives and antimicrobial materials that can prevent the growth of undesired bacteria and other micro-organisms. The surfaces are coated with microsized or nanosized silver particles to offer protection against bacteria, fungi, and other unwanted germs. U.S. Pat. Nos. 6,984,392 and 7,476,698 assigned to Bio Gate AG describes certain formulations of anti-microbial coatings.

Others have disclosed anti-microbial coatings which may be suitable, including Boston Scientific Scimed, Inc. of Maple Grove, Minn. in U.S. Pat. No. 7,635,358 and I-Flow Corp. of Lake Forest, Calif. in U.S. Pat. No. 7,547,302, whose disclosures are expressly incorporated herein by reference. The Boston Scientific patent proposes a substrate formed from the anti-microbial agent such as an iodine-polycarbonate material. The I-Flow patent discloses anti-microbial layers or materials configured to provide the sustained release of anti-microbial agents. The anti-microbial layer or material may be a heavy metal such as gold, platinum, silver, zinc or copper, including heavy metal ions. Other anti-microbial substances may also be used such as antibiotics or germicidal chemicals. Of course, these are just a few examples, and numerous other suitable anti-microbial coatings or agents may be used in the present application.

It should also be mentioned that anti-microbial coatings or agents are desirable not just for the glaucoma shunts described herein, but also for other glaucoma shunts for relieving intraocular pressure. For instance, devices that create a direct passage from the anterior chamber to the conjunctiva, such as the Ex-PRESS Mini Glaucoma Shunt from Optonol of Neve Ilan, Israel, may benefit from an antimicrobial coating to help prevent infection post-op. Another type of device that would likely be improved with an anti-microbial coating is a micro filter on the outer end of a drainage tube inserted into the anterior chamber, such as that disclosed in U.S. Pat. No. 7,641,627 to Camras. Finally, devices that create a bridge between the supraciliary space and the anterior chamber, such as the SOLX® Gold Shunt, may be improved with the addition of an anti-microbial coating. The SOLX device can be seen in U.S. Pat. No. 7,207,965.

Each of the aspects disclosed herein may be used in combination with one or more of the others to provide an improved glaucoma shunt. For instance, a desirable glaucoma shunt may have a pliable plate with a decreased surface area in accordance with the principles described above and at least 8 fenestration holes, microtexturing on an outer or inner face and also on the elastomeric drainage tube, an inner tube lumen having a radius of less than 50 microns, a flow restrictor that either dissolves or is movable in the drainage tube, and an anti-microbial coating on at least the lumen of the drainage tube. This is just one example, and many other permutations are possible. In general, the improved glaucoma shunts will produce a lower bleb height, which reduces any detrimental interaction with eye muscle coordination. The improved shunt will also effectively regulate IOP, and prevent endophthalmitis.

While the invention has been described in its preferred embodiments, it is to be understood that the words which have been used are words of description and not of limitation. Therefore, changes may be made within the appended claims without departing from the true scope of the invention.

What is claimed is:

1. An implantable glaucoma shunt for treating glaucoma in an eye, comprising:
   a plate adapted to be positioned on the sclera and having an effective surface area $A_{eff}$ of 250 mm² or less, the plate also having at least 8 fenestrations extending between an outer face and an inner face; and
   an elastomeric drainage tube having an outflow end connected to the plate and opening at the outer face thereof, and an inflow end extending away from the plate, the drainage tube having an open lumen and a length sufficient to extend into the anterior chamber of the eye,
   wherein the plate has microtexturing on at least an outer or an inner face comprising an average peak-to-valley depth normal to the outer face of between about 0.5-10 microns.

2. The glaucoma shunt of claim 1, wherein the effective surface area of the plate ($A_{eff}$) is determined by the formula $A_{eff}=A+G$, where:
   A=the tissue area surrounding the plate being around 200-400 mm², and
   G=a reduction in effective plate surface area determined by:

$$G=M(\pi R^2)-M(2\pi RB)$$

where:
   M=number of fenestration holes,
   R=radius of fenestration holes, and
   B=bleb height.

3. The glaucoma shunt of claim 1, wherein both the inner and outer faces have the microtexturing, and the microtexturing is provided in different patterns on the inner and outer faces.

4. The glaucoma shunt of claim 1, wherein the microtexturing is further provided on the exterior of the elastomeric drainage tube.

5. The glaucoma shunt of claim 1, wherein the drainage tube has a coating of antimicrobial material within its lumen.

6. The glaucoma shunt of claim 1, further including a flow restrictor positioned within the drainage tube having an open throughbore smaller than the lumen.

7. The glaucoma shunt of claim 1, further including a flow restrictor positioned within the drainage tube and being movable therein, the flow restrictor having exterior length markings and a length sufficient to extend from within the drainage tube to a location past a bleb that forms over the plate after implant.

8. An implantable glaucoma shunt for treating glaucoma in an eye, comprising:
   a plate adapted to be positioned on the sclera; and
   an elastomeric drainage tube having an outflow end connected to the plate and opening at the outer face thereof, and an inflow end extending away from the plate, the drainage tube having an open lumen and a length sufficient to extend into the anterior chamber of the eye, the inner lumen of the tube having a radius of less than 50 microns.

9. The glaucoma shunt of claim 8, wherein the inner tube lumen radius is less than 50 microns and greater than or equal to a magnitude determined by the following formula:

$$r=(8\eta L/\pi R)^{0.25}$$

where:
   average aqueous resistance R=3.333 mmHg/microliter/minute,
   1 mmHg=133.3 Pa (kgm/s²),
   1 microliter/minute=1,667×10⁻¹¹ m³/s,
   L=length of tube (mm),
   average aqueous resistance R=2.666×10¹³ kg/sm², and
   dynamic viscosity h=7.50×10⁻⁴ kg/sm.

10. The glaucoma shunt of claim 8, wherein the plate has microtexturing on at least an outer or an inner face comprising an average peak-to-valley depth normal to the outer face of between about 0.5-10 microns.

11. The glaucoma shunt of claim 10, wherein both the inner and outer faces have the microtexturing, and the microtexturing is provided in different patterns on the inner and outer faces.

12. The glaucoma shunt of claim 10, wherein the microtexturing is further provided on the exterior of the elastomeric drainage tube.

13. The glaucoma shunt of claim 8, wherein the drainage tube has a coating of antimicrobial material within its lumen.

14. The glaucoma shunt of claim 8, further including a flow restrictor positioned within the drainage tube having an open throughbore smaller than the lumen.

15. The glaucoma shunt of claim 8, further including a flow restrictor positioned within the drainage tube and being movable therein, the flow restrictor having exterior length markings and a length sufficient to extend from within the drainage tube to a location past a bleb that forms over the plate after implant.

* * * * *